US006884597B1

(12) United States Patent
Taya et al.

(10) Patent No.: US 6,884,597 B1
(45) Date of Patent: Apr. 26, 2005

(54) METHOD FOR DETECTING ACETYLTRANSFERASE AND DEACETYLASE ACTIVITIES AND METHOD FOR SCREENING INHIBITORS OR ENHANCERS OF THESE ENZYMES

(75) Inventors: Yoichi Taya, Tokyo (JP); Katsuyuki Tamai, Ina (JP); Toshiaki Miyazaki, Ina (JP)

(73) Assignee: Medical & Biological Laboratories, Co., Ltd., Aichi (JP)

( * ) Notice: Subject to any disclaimer, the term of this patent is extended or adjusted under 35 U.S.C. 154(b) by 0 days.

(21) Appl. No.: 09/618,424

(22) Filed: Jul. 18, 2000

Related U.S. Application Data

(63) Continuation-in-part of application No. PCT/JP99/00191, filed on Jan. 20, 1999.

(30) Foreign Application Priority Data

Jan. 20, 1998 (JP) .......................................... 10-009171

(51) Int. Cl.[7] ....................... G01N 33/53; G01N 33/543

(52) U.S. Cl. ........................... 435/7.92; 435/4; 435/7.1; 435/7.5; 435/7.9; 435/15; 435/175; 435/177; 435/178; 435/180; 435/193; 435/810; 435/814; 435/969; 435/975; 436/63; 436/86; 436/172; 436/518; 436/528; 436/529; 436/800; 436/805; 436/815; 436/823

(58) Field of Search ............................. 435/4, 7.1, 7.5, 435/7.9, 7.92, 15, 175, 177, 178, 180, 193, 810, 814, 969, 975; 436/63, 86, 172, 518, 528, 529, 800, 805, 815, 823, 164

(56) References Cited

U.S. PATENT DOCUMENTS

| | | | | |
|---|---|---|---|---|
| 5,364,764 A | * 11/1994 | Haugland et al. | ............. | 435/15 |
| 5,830,672 A | * 11/1998 | Wainer et al. | ............... | 435/7.9 |
| 5,902,727 A | * 5/1999 | Roth et al. | .................. | 435/7.21 |
| 5,955,269 A | * 9/1999 | Ghai et al. | ...................... | 435/6 |
| 6,017,744 A | * 1/2000 | Hillman et al. | ............. | 435/193 |

FOREIGN PATENT DOCUMENTS

| | | |
|---|---|---|
| JP | 5-500007 | 1/1993 |
| JP | 7-107983 | 4/1995 |
| WO | WO 91/02080 | 2/1991 |
| WO | WO 95/03701 | 2/1995 |
| WO | WO 96/30762 | 10/1996 |
| WO | WO 97/02360 | 1/1997 |

OTHER PUBLICATIONS

Poethke et al. Establishment of an efficient enzyme–linked immunosorbent assay for the determination of a human choline acetyltransferase. Journal of Neuroimmunology. (1997) vol. 76, Nos. 1–2, pp. 206–212.*
T. Hebbes et al., *Molecular Immunology*, 26(9):865–873 (1989).
D. Penque et al., *Eur. J. Biochem.*, 195:487–494 (1991).
Y. Chiang et al., *The Journal of Biological Chemistry*, 271(50):32359–32365 (1996).
C. Patrono, TiPS, 10: 453–458 (1989).
Pfeffer et al., J. Biol. Chem., 261:2496–2498, (1986).
Turner et al., Eur. J. Biochem., 179:131–1139 (1989).
Couppez et al., J. Biol. Chem., 262:2854–2860 (1987).
Scolnick et al., Cancer Res., 57:3693–3696 (1997).
Medina et al., Cancer Res., 57:3697–3707 (1997).
Hendzel et al., J. Biol. Chem., 266:21936–21942 (1991).
Yang et al., J. Biol. Chem., 272:28001–28007 (1997).
Yoshida et al., J. Biol. Chem., 265:17174–17179 (1990).
Kijima et al., J. Biol. Chem., 268:22429–22435 (1993).
Muller et al., Molec. Immun., 24:779–789 (1993).
Brownell et al., Proc. Natl. Acad. Sci. U.S.A., 92:6364–6368 (1995).
Chen et al., Proc Natl. Acad. Sci. U.S.A., 94:5798–5803 (1997).
Yang et al., Proc. Natl. Acad. Sci. U.S.A., 93:12845–12850 (1996).
Rundlett et al., Proc. Naltl. Acad. Sci. U.S.A., 93:14503–14508 (1996).
Candau et al., EMBO J., 16L555–565 (1997).
Hebbes et al., EMBO J., 7:1395–1402 (1988).
Roth et al., Cell, 87:5–8 (1996).
Ogryzko et al., Cell, 87:953–959 (1996).
Hassig et al., Cell, 89:341–347 (1997).
Laherty et al., Cell, 89:349–356 (1997).
Gu et al., Cell, 90:595–606 (1997).
Mizzen et al., Cell, 87:1261–1270 (1996).
Schekman et al., Cell, 87:595–595 (1996).
Lusser et al., Science, 277:88–91 (1997).
Taunton et al., Science, 272:408–411 (1996).
Kuo et al., Nature, 383:269–272 (1996).
Bannister et al., Nature, 384:641–643 (1996).
Gu et al., Nature, 387:819–822 (1997).
Lill et al., Nature, 387:823–826 (1997).
Yang et al., Nature, 382:319–324 (1996).

* cited by examiner

*Primary Examiner*—Long V. Le
*Assistant Examiner*—Kartic Padmanabhan
(74) *Attorney, Agent, or Firm*—Peter F. Corless; Christine C. O'Day; Edwards & Angell, LLP

(57) ABSTRACT

A method for simply and conveniently detecting acetyltransferase and deacetylase activities of proteins by executing an acetylation reaction of a peptide substrate with an acetyltransferase, or a deacetylation reaction of an acetylated peptide substrate with a deacetylase, and after the completion of these reactions, detecting the acetyl group bound to the peptide substrate by using an anti-acetylated peptide antibody. This system for detecting acetyltransferase and deacetylase activities using the anti-acetylated peptide antibody enables screening inhibitors or enhancers of acetyltransferase and deacetylase. A system for screening deacetylase inhibitors or acetyltransferase enhancers using cultured cells is also provided.

7 Claims, 16 Drawing Sheets

SEQUENCE LISTING

```
<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<221> NAME/KEY: MOD_RES
<222> LOCATION: (7)
<223> OTHER INFORMATION: ACETYLATION
<220> FEATURE:
<223> OTHER INFORMATION: Description of Artificial Sequence: Artificial
      Sequence

<400> SEQUENCE: 1

Ser Thr Ser Arg His Lys Lys Leu Met Phe Lys Thr Glu Cys
  1               5                  10


<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Artificial
      Sequence

<400> SEQUENCE: 2

Ser Thr Ser Arg His Lys Lys Leu Met Phe Lys Thr Glu Cys
  1               5                  10


<210> SEQ ID NO 3
<211> LENGTH: 14
<212> TYPE: PRT
<213> ORGANISM: Artificial Sequence
<220> FEATURE:
<221> NAME/KEY: MOD_RES
<222> LOCATION: (7)
<223> OTHER INFORMATION: ACETYLATION
<220> FEATURE:
<223> OTHER INFORMATION: Description of Artificial Sequence: Artificial
      Sequence

<400> SEQUENCE: 3

Ser His Leu Lys Ser Lys Lys Gly Gln Ser Thr Ser Arg Cys
  1               5                  10


<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Artificial
      Sequence

<400> SEQUENCE: 4
```

-continued

```
Ser His Leu Lys Ser Lys Lys Gly Gln Ser Thr Ser Arg Cys
  1               5                  10


<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 5

gcgggatccc agaataggta tcattctgt gag                                  33


<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 6

agactcgagc ttgcactcgt tgcaggtgta gac                                 33


<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 7

tatggatcca tgctggagga ggagatctat g                                   31


<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 8

tatctcgagc ttgtcaatga ggcctccctc c                                   31


<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 9

cgcggatcca tggcgcagac gcagggcacc                                     30


<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 10
```

-continued

```
cgcctcgagg gccaacttga cctcctcctt                                    30


<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 11

cgcggatcca tggccaagac cgtggcgtat                                    30


<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 12

cgcctcgaga atctccacat cgctttcctt                                    30


<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Artifical
      Sequence

<400> SEQUENCE: 13

Ser Thr Ser Arg His Lys Lys Leu Met Phe Lys Thr Glu
  1               5                  10


<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Artifical
      Sequence

<400> SEQUENCE: 14

Ser His Leu Lys Ser Lys Lys Gly Gln Ser Thr Ser Arg
  1               5                  10


<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 15

tatggatcca agaggaagag aatctccgc                                     29


<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Artificially synthesized primer sequence
```

-continued

<400> SEQUENCE: 16
tatctcgagg tctgagtcag gcccttctga 30

<210> SEQ ID NO 17
<211> LENGTH: 13
<212> TYPE: PRT
<213> ORGANISM: Artificial Sequence
<220> FEATURE:
<221> NAME/KEY: MOD_RES
<222> LOCATION: (7)
<223> OTHER INFORMATION: ACETYLATION
<220> FEATURE:
<223> OTHER INFORMATION: Description of Artificial Sequence: Artificial Sequence

<400> SEQUENCE: 17

Ser Thr Ser Arg His Lys Lys Leu Met Phe Lys Thr Glu
1 5 10

<210> SEQ ID NO 18
<211> LENGTH: 13
<212> TYPE: PRT
<213> ORGANISM: Artificial Sequence
<220> FEATURE:
<221> NAME/KEY: MOD_RES
<222> LOCATION: (7)
<223> OTHER INFORMATION: ACETYLATION
<220> FEATURE:
<223> OTHER INFORMATION: Description of Artificial Sequence: Artificial Sequence

<400> SEQUENCE: 18

Ser His Leu Lys Ser Lys Lys Gly Gln Ser Thr Ser Arg
1 5 10

<210> SEQ ID NO 19
<211> LENGTH: 21
<212> TYPE: PRT
<213> ORGANISM: Artificial Sequence
<220> FEATURE:
<221> NAME/KEY: MOD_RES
<222> LOCATION: (5)
<223> OTHER INFORMATION: ACETYLATION
<220> FEATURE:
<221> NAME/KEY: MOD_RES
<222> LOCATION: (8)
<223> OTHER INFORMATION: ACETYLATION
<220> FEATURE:
<221> NAME/KEY: MOD_RES
<222> LOCATION: (12)
<223> OTHER INFORMATION: ACETYLATION
<220> FEATURE:
<221> NAME/KEY: MOD_RES
<222> LOCATION: (16)
<223> OTHER INFORMATION: ACETYLATION
<220> FEATURE:
<223> OTHER INFORMATION: Description of Artificial Sequence: Artificial Sequence

<400> SEQUENCE: 19

Ser Gly Arg Gly Lys Gly Gly Lys Gly Leu Gly Lys Gly Gly Ala Lys
1 5 10 15

Arg His Arg Lys Cys
20

<210> SEQ ID NO 20
<211> LENGTH: 21
<212> TYPE: PRT
<213> ORGANISM: Artificial Sequence
<220> FEATURE:

-continued

```
<223> OTHER INFORMATION: Description of Artificial Sequence: Artifical
      Sequence

<400> SEQUENCE: 20

Ser Gly Arg Gly Lys Gly Gly Lys Gly Leu Gly Lys Gly Gly Ala Lys
  1               5                  10                  15

Arg His Arg Lys Cys
            20
```

METHOD FOR DETECTING ACETYLTRANSFERASE AND DEACETYLASE ACTIVITIES AND METHOD FOR SCREENING INHIBITORS OR ENHANCERS OF THESE ENZYMES

The present application is a continuation-in-part of International Application No. PCT/JP99/00191, filed on Jan. 20, 1999.

TECHNICAL FIELD

The present invention relates to a method for detecting acetyltransferase and deacetylase activities by using an anti-acetylated peptide antibody, a method for screening inhibitors or enhancers of acetyltransferase and deacetylase, and a kit for detecting and screening these enzymes.

BACKGROUND ART

A protein is synthesized (transcription and translation) based on the nucleotide information of DNA, the entity of a gene. It is known that activities and functions in most proteins are regulated by further modification after translation. Phosphorylation is one of the most investigated posttranslational modifications of proteins. Many of the oncogene family proteins, such as c-Src and c-Raf, which manage intracellular signal transduction are regulated by phosphorylation and dephosphorylation, and these intracellular signal transductions themselves are conduced by a sequence of phosphorylation and dephosphorylation (Morrison, D. K., Kaplan, D. R. et al. (1989) Cell 58, 649–657; Howe, L. R., Leevers, S. J. et al. (1992) Cell 71, 335–342; Kolch, W., Heidecker, G. et al. (1993) Nature 364, 249–252; Dent, P., Jelinek, T. et al. (1995) Science 268, 1902–1906). Even in the nucleus of a cell, many transcription factors and their regulatory proteins are known to be minutely regulated by phosphorylation and dephosphorylation (Hill, C. S., Marais, R. et al. (1993) Cell 73, 395–406; Sanchez, I., Hyghes, R. T. et al. (1994) Nature 372, 794–798; Akoulitchev, J., Makela, T. P. et al. (1995) Nature 377, 447–560; Weinberg, R. A. (1995) Cell 81, 323–330). As another posttranslational modification, many extracellular proteins and cell-surface proteins, such as receptors, have been reported to be subjected to glycosylation, such as the addition of a glycosyl group (Guan, J. L., Machamer, C. E. and Rose, J. K. (1985) Cell 42, 489–496; Sairam, M. R. and Bhargavi, G. N. (1985) Science 229, 65–67; Diamond, M. S., Staunton, D. E et al. (1991) Cell 65, 961–971; Entwistle, J., Hall, C. L. and Turley, E. A. (1996) J. Cell. Biochem. 61, 569–577). Such glycosylations are proposed to have an important role in the formation of the higher-order structure of the extracellular matrix and cell-surface receptors, and intercellular recognition. GTP binding protein family, such as Ras, has been known to be modified with lipids by farnesylation and addition of palmitic acid (Willumsen, B. M., Christensen A. et al. (1984) Nature 310, 583–586; Buss, J. E., Solski, P. A. et al. (1989) Science 24, 1600–1603; Lowy, D. R. and Willumsen, B. M. (1989) Nature 341, 384–385; Vogt, A., Qian, Y et al. (1995) J. Biol. Chem. 270, 660–664). These modifications are thought to be important for the localization of proteins into the cell membrane and the interaction with other proteins.

Acetylation has been reported as a posttranslational modification only in histone. Histone is a basic protein binding to DNA and forms a nucleosome, the basic structural unit of chromatin. It was reported that this protein is highly acetylated at activated chromatin sites, where mRNA is actively transcribed, while the acetylation level is low at inactivated chromatin sites (Hebbes, T. R., Throne, A. W. and Crane-Robinson, C. (1988) EMBO J. 7, 1395–1402; Wolffe, A. P. (1996) Science 272, 371–372). As enzymes which transfer an acetyl group to histone from acetyl CoA in mammalian cells (histone acetyltransferase: HAT), five kinds; GCN5 (Kuo, M.-H., Brownell, J. E. et al. (1996) Nature 383, 269–272; Brownell, J. E., and Allis, C. D. (1996) Curr. Opin. Genet. Dev. 6, 176–184; Candau, R., Zhou, JX., Allis, C. D. and Beregr, S. L. 1997) EMBO J. 16, 555–565), P/CAF (Ogryzko, V. V., Sciltz, R. L., Russanova, V., Howard, B. H., and Nakatani, Y. (1996) Cell 87, 953–959) p300/CBP (Bannister, A. J., and Kouzarides. T. (1996) Nature 384, 641–643; Yang, X.-J., Ogryzko, V. V. et al. (1996) Nature 382, 319–382), TAFII250 (Mizzen, C. A., Yang, X.-Y. et al. (1996) Cell 87, 1261–1270), Tip60 (Kimura, A., Yamamoto, Y., Horikosi, M., Institute of Molecular and Cellular Biosciences, Laboratory of Developmental Biology, the University of Tokyo, Analysis of a novel histone acetyltransferase Tip60 family, presented at The Twentieth Annual Meeting of Japanese Society of Molecular Biology, Dec. 17, 1997) have been reported. As enzymes which deacetylate histone (histone deacetylase), three genes; HDAC1/RPD3 (Taunton, J., Hassig, C. A., and Schreiber, S. L. (1996) Science 272, 408–411; Rundlett, S. E., Carmen, A. A. et al. (1996) Proc. Natl. Acad. Sci. USA. 93, 14503–14508), HDAC2/YY-1BP (Yang, W.-M., Inouye, C., zeng, Y. Y., Bearss, D., and Seto, E. (1996) Proc. Natl. Acad. Sci. USA. 93, 12845–12850: Lusser, A., Brosch, G. et al. (1997) Science277, 88–91), HDAC3 (Yang, W.-M., Yao, Y.-L., Sun, J.-M., Davie, J. R., and Seto, E. (1997) J. Biol. Chem. 272, 28001–28007), have been reported.

Recently, it was reported that p300/CBP reported as a HAT, acetylates not only histone, but also p53, enhancing p53 activity (Scolinick, D. M., Chehab, N. H. et al. (1997) Cancer Res 57, 3693–3696; Gu, W., Shi, X.-L., and Roeder, R. G. (1997) Nature 387, 819–823; Lill, N. L., Grossman S. R. et al. (1997) Nature 387, 823–827; Gu, W., and Roeder, R. G. (1997) Cell 90, 595–606). p53 had been identified as an intranuclear protein specifically and highly expressed in cancerous cells, and was thought to be an oncogene by experiments such as transduction experiments using p53 gene isolated from cancerous cells. However, p53 gene isolated from cancerous cells was identified to be a mutant, and it was found that the normal p53 gene is in fact a cancer suppressor gene because the normal p53 gene shows phenotypes of inhibiting cellular proliferation, arresting the cell cycle, and inducing cell death, etc. It is proposed that expression of p53 is induced by DNA damage and such, and functions as a transcriptional factor by binding to a specific sequence of DNA, illustrating the function as a cancer suppressor gene. Binding ability of p53 to a specific DNA is enhanced by acetylation, and as a result, transcriptional activation is also elevated. It has been also reported that transcriptional activity of p53 is controlled by phosphorylation. The report that acetylation strongly induces enhancement of transcriptional activity of p53 implies not only the existence of a novel regulatory mechanism, but also the possibility that acetylation, like phosphorylation, is involved in the control of protein function not only in histone but in cells in general. Thus, enzymes relating to phosphorylation, dephosphorylation and lipid modifications, and their substrate-proteins have received wide attention recently as targets in development of novel drugs such as immune inhibitors and anticancer agents. Screening for inhibitors against these enzymes are underway.

Considering the circumstances, acetylation, deacetylation and their relating proteins are expected to be new targets in drug development in the future. So far, drugs such as sodium butyrate, trichostatin A, and trapoxin, have been reported as inhibitors for histone deacetylase. These inhibitors have been originally identified as antifungal agents or morphological normalization substances for v-sis-transformant cells, causing arrest of the cell cycle and induction of cell differentiation (Taunton, J., Hassig, C. A., and Schreiber, S. L. (1996) Science 272, 408–411; Yoshida, M., Kijima, M., Akita, M., and Beppu, T. (1990) J. Biol. Chem. 265, 17174–17179; Kijima, M., Yoshida, M. and et al. (1993) J. Biol. Chem. 268, 22429–22435; Chen, W, Y., Bailey, E. C. et al. (1997) Proc Natl. Acad. Sci. USA, 94, 5798–5803; Medina, V., Edmonds, B. et al. (1997) Cancer Res. 57; 3697–3707). Later studies demonstrated that the target of these drugs is histone deacetylase. These kinds of inhibitors are expected to function as anticancer drugs and antimicrobial agents, and screening of histone deacetylase inhibitors as a search for substances comprising a similar function is expected to be carried out in the future.

The methods known for measuring the acetyltransferase and deacetylase activities are, however, very cumbersome. Specifically, to measure acetyltransferase activity, acetyltransferase and radiolabeled acetyl CoA are added to histone purified from cells or a synthetic peptide substrate to execute the acetyl group-transferring reaction. Each reaction solution is then transferred onto a filter and washed to measure enzyme activity using a liquid scintillation counter (Bannister, A. J., and Kouzarides. T. (1996) Nature 384, 641–643; Mizzen, C. A., Yang, X.-Y et al. (1996) Cell 87, 1261–1270; Gu, W., and Roeder, R. G. (1997) Cell 90, 595–606; Brownell, J. E. and Allis, C. D. (1995) Proc. Natl. Acad. Sci. USA 92, 6364–6368). To measure the deacetylase activity, radiolabeled acetic acid is added into a medium of cultured cells to metabolically radiolabel cellular histone. Histone is purified from the cells, and deacetylase is reacted to the histone for the deacetylation reaction. After the completion of the reaction, radiolabeled acetyl group which is released from histone is isolated and extracted with ethyl acetate to measure the enzyme activity by a liquid scintillation counter (Laherty, C. D., Yang, W.-M. et al. (1997) Cell 89, 349–356; Hassig, C., Fleischer, T. C. et al. (1997) Cell 89, 341–347; Hendzel, M. J., Delcuve, G. P. and Davie,-J. R. (1991) J. Bio. Chem. 32, 21936–21942).

These measurement systems are so cumbersome that assaying many samples under numerous conditions is difficult. Therefore, a simple and convenient screening system for new drug development and such was desired.

DISCLOSURE OF THE INVENTION

An objective of the present invention is to provide a method for conveniently detecting acetyltransferase and deacetylase activities, a method for conveniently screening inhibitors or enhancers for acetyltransferase and deacetylase, and a kit for detecting and screening these.

As a result of strenuous research to solve the above problems, the present inventors came upon the idea of using an antibody specifically binding to an acetylated peptide (an anti-acetylated peptide antibody) for the detection of the acetyltransferase and deacetylase activities. Thus, an anti-acetylated peptide antibody was prepared, and the acetylation reaction of a peptide substrate by acetyltransferase, and the deacetylation reaction of an acetylated peptide substrate by deacetylase were executed. After the completion of the reactions, the acetyl group bound to the peptide substrate was detected. As a result, the present inventors found that the acetyltransferase and deacetylase activities of proteins can be conveniently detected by using an anti-acetylated peptide antibody.

Moreover, the present inventors discovered that inhibitors and enhancers for acetyltransferase and deacetylase could be conveniently screened by using the system for detecting the acetyltransferase and deacetylase activities utilizing the anti-acetylated peptide antibody.

Further, the present inventors succeeded in developing a system for screening inhibitors for deacetylase, or enhancers for acetyltransferase by using cultured cells.

The present invention relates to a method for detecting acetyltransferase and deacetylase activities by using an anti-acetylated peptide antibody, a method for screening inhibitors and enhancers for acetyltransferase and deacetylase, and a kit for detecting or screening these, and more specifically relates to:

(1) a method for detecting the acetyltransferase activity in a test peptide, comprising the steps of:
(a) contacting a test peptide with a peptide substrate, and,
(b) detecting an acetyl group binding to the peptide substrate using an anti-acetylated peptide antibody;
(2) a method for screening a compound that inhibits or enhances the activity of acetyltransferase, comprising the steps of:
(a) contacting acetyltransferase with a peptide substrate in the presence of a test compound,
(b) detecting an acetyl group binding to the peptide substrate using an anti-acetylated peptide antibody, and,
(c) screening a compound that decreases or increases the detected amount of the acetyl group binding to the peptide substrate in comparison with the amount in the absence of the test compound;
(3) a method for detecting the deacetylase activity in a test peptide, comprising the steps of:
(a) contacting the test peptide with an acetylated peptide substrate, and,
(b) detecting an acetyl group binding to the substrate peptide using an anti-acetylated peptide antibody;
(4) a method for screening a compound that inhibits or enhances the deacetylase activity, comprising the steps of:
(a) contacting deacetylase with an acetylated peptide substrate in the presence of a test compound,
(b) detecting an acetyl group binding to the peptide substrate using an anti-acetylated peptide antibody, and,
(c) screening a compound that decreases or increases the detected amount of the acetyl group binding to the peptide substrate in comparison with the amount in the absence of the test compound;
(5) the method of any one of (1) to (4), wherein the peptide substrate is p53;
(6) the method of any one of (1) to (4), wherein the peptide substrate is labeled;
(7) the method of (6), wherein the label is biotin;
(8) the method of any one of (1) to (4), wherein the peptide substrate is immobilized on a solid phase;
(9) the method of any one of (1) to (4), wherein the anti-acetylated peptide antibody is labeled;
(10) the method of any one of (1) to (4), wherein the acetyl group binding to the peptide substrate is detected by ELISA;
(11) a method for screening a compound that inhibits the deacetylase activity or a compound that enhances the activity or expression of acetyltransferase, comprising the steps of:
(a) contacting a test compound with cultured cells,
(b) immobilizing said cultured cells,
(c) detecting an acetyl group on a specific protein in said cultured cells using an anti-acetylated peptide antibody, and, (d) screening a compound that increases the acetyl group on said specific protein in comparison with a control untreated with the test compound;

(12) a method for screening a compound that inhibits the deacetylase activity of histone or a compound that enhances the activity or expression of acetyltransferase of histone, comprising the steps of:

(a) providing cultured cells carrying a vector comprising a promoter that functions within cultured cells and a reporter gene ligated to the downstream of said promoter, (b) contacting a test compound with said cultured cells, and, (c) screening a compound that increases the reporter activity, in comparison with a control untreated with the test compound;

(13) a compound isolable by any one of the screening method of (2), (4), (11), and (12);

(14) the compound of (13), wherein the compound is derived from nature;

(15) a kit for the detecting or screening method of any one of (1) to (4), and (11), comprising an anti-acetylated peptide antibody.

In the present invention, a "peptide" means a compound composed of two or more amino acids which are bound through a peptide bond, without any limitation of the chain length. Therefore, a peptide of the present invention also includes a protein. In the present invention, "acetyltransferase" means an enzyme which catalyses the reaction that transfers an acetyl group ($CH_3CO$—) from one substance (for example, acetyl CoA) to another. A "deacetylation enzyme" means an enzyme which releases an acetyl group from a specific substance. An "anti-acetylated peptide antibody" means an antibody specifically binding to an epitope including an acetylated amino acid residue or to a specific acetylated amino acid (for example, an acetylated lysine).

The first aspect of the present invention is a method for detecting the acetyltransferase activity by using an anti-acetylated peptide antibody. The method for detecting the acetyltransferase activity of the present invention comprises the steps of: (a) contacting a test peptide with a peptide substrate, and (b) detecting an acetyl group binding to the peptide substrate using an anti-acetylated peptide antibody.

The test peptide is not particularly limited. Any peptide whose acetyltransferase activity needs to be detected can be used. As a peptide substrate, any desired peptide expected to be acetylated by a test peptide can be used. The test peptide and the peptide substrate can be a natural, genetically engineered, or synthetic peptide. They can be fused with another peptide (for example, glutathione-S-transferase) for the purpose of, for example, the convenient purification of peptides. They can be known or novel peptides. Examples of known acetyltransferases are, GCN5 (Kuo, M. -H., Brownell, J. E. et al. (1996) Nature 383, 269–272; Brownell, J. E., and Allis, C. D. (1996) Curr. Opin. Genet. Dev. 6, 176–184; Candau, R., Zhou, JX., Allis, C. D. and Berger, S. L. (1997) EMBO J. 16, 555–565), P/CAF (ogryzko, V. V., Sciltz, R. L., Russanova, V., Howard, B. H., and Nakatani, Y. (1996) Cell 87, 953–959), p300/CBP (Bannister, A. J., and Kouzarides. T. (1996) Nature 384, 641–643; Yang, X.-J., Ogryzko, V. V. et al. (1996) Nature 382, 319–382; Scolinick, D.-M., Chehab, N. H. and et al. (1997) Cancer Res. 57, 3693–3696; Gu, W., Shi, X.-L., and Roeder, R. G. (1997) Nature 387, 819–823; Lill, N. L., Grossman, S. R. et al. (1997) Nature 387, 823–827; Gu, W., and Roeder, R. G. (1997) Cell 90, 595–606), TAFII250 (Mizzen, C. A., Yang, X.-Y. et al. (1996) Cell 87, 1261–1270), Tip 60 (Kimura A., Yamamoto Y., Horikosi M., Institute of Molecular and Cellular Biosciences, Laboratory of Developmental Biology, the University of Tokyo, Analysis of a novel histone acetyltransferase Tip60 family, presented at The Twentieth Annual Meeting of Japanese Association of Molecular Biology) and such. Examples of peptides known or expected to be acetylated are, p53 (Gu, W. and Roeder, R. G. (1997) Cell 90, 595–606), histone (H1, H2A, $H_2B$, H3, H4) (Couppez, M., Ponthieu, A. M. and Sautiere, P. (1987) J. Bio. Chem. 262, 2854–2860; Hebbes, T. R., Throne, A. W. and Robinson, C. C. (1988) EMBO J. 7, 1395–1402; Roth, S. Y., and Allis, C. D. (1996) Cell 87, 5–8), TFIIE (Gu, W. and Roeder, R. G. (1997) Cell 90, 595–606), TFIIF (Gu, W. and Roeder, R. G. (1997) Cell 90, 595–606), PC4 (Gu, W. and Roeder, R. G. (1997) Cell 90, 595–606) and these can be utilized.

A test peptide can be contacted with a peptide substrate in the liquid or solid phase. In the case of contacting in the liquid phase, a peptide substrate can be labeled with a labeling agent such as biotin. When a peptide substrate labeled with biotin is used, after contacting with a test peptide, the reaction mixture is added to a support sensitized with streptoavidin (refer to FIG. 1). Any substances with an affinity to each other can be applied in the present invention besides the avidin-biotin system. While in the case of contacting in the solid phase, the contact reaction is executed on an immobilized peptide substrate (refer to FIG. 2). In the contact reaction, a compound having an acetyl group, for example, acetyl CoA, is added to the reaction system.

A method for detecting the acetyltransferase activity is characterized by using an anti-acetylated peptide antibody for detecting an acetyl group bound to a substrate. An anti-acetylated peptide antibody, can be monoclonal or polyclonal. These antibodies can be prepared by the methods known to a person skilled in the art (for example, refer to Cell Biology, Supplement, Protocol for Anti-Peptide Antibody Experiment, 1994, Shujun-Sha; Turner, B. M. and Fellows, G. (1989) Eur J. Biochem. 179, 131–139; Muller, S., Isabey, A. et al. (1987) Molecular Immunology 24, 779–789; Pfeffer, U., Ferrari, N. and Vidali, G. (1989) J. Bio. Chem. 261, 2496–2498).

For detecting an acetylated peptide substrate, an anti-acetylated peptide antibody is appropriately labeled for use. Any label comprising a detectable sensitivity, for example, an enzyme label, such as peroxidase, β-D-galactosidase, alkaline phosphatase, glucose-6-phosphate dehydrogenase, acetylcholinesterase, etc., and a fluorescent label, such as delphinium, etc., a radioactive label, etc., can be used. Detection can be conducted by labeling a substance specifically binding to an anti-acetylated peptide antibody, for example, a second antibody, protein A, protein G, protein A/G (a fused protein of A and G), etc., without labeling an anti-acetylated peptide antibody. An acetyl group binding to a peptide substrate can be detected by methods known to a person skilled in the art, depending on the labels described above (refer to, for example, ultra sensitive enzyme immunoassay, Ishikawa E., Gakkai Shuppan Center, 1993). As a result, if a significant detection of the acetyl group on a peptide substrate is seen, it indicates the acetyltransferase activity in a test peptide.

In the present invention, an anti-acetylated peptide antibody can be used for detecting not only the acetyltransferase activity, but also the deacetylase activity in a test peptide. Therefore, the present invention relates to a method for detecting the deacetylase activity by using an anti-acetylated peptide antibody. The method for detecting the deacetylase activity of the present invention comprises the steps of: (a) contacting a test peptide with an acetylated peptide substrate, and (b) detecting an acetyl group binding to a peptide substrate using an anti-acetylated peptide antibody.

Any peptide can be used as the test peptide. A peptide for whose deacetylase activity needs to be detected can be used. As a peptide substrate, a desired acetylated peptide which is expected to be deacetylated by a test peptide can be used. The test peptide and the peptide substrate can be a natural, genetically engineered, or synthetic peptide. A peptide can be fused with another peptide (for example, glutathione-S-transferase) for convenience of purifying peptides, etc. They can be known or novel peptides. As known deacetylases, for example, HDAC1/RPD3 (Taunton, J., Hassig, C. A., and Schreiber, S. L. (1996) Science 272, 408–411, Rundett, S. E., Carmen, A. A., et al. (1996) Proc. Natl. Acad. Sci. USA, 93, 14503–14508), HDAC2/YY-1BP (Yang, W.-M., Inouye, C., Zeng, Y. Y. Bearss, D., and Seto, E. (1996) Proc. Natl. Acad. Sci. USA. 93, 12845–12850; Lusser, A., Brosch, G. et al.(1997) Science 277,88–91), HDAC3 (Yang, W.-M., Yao, Y.-L., Sun, J.-M., Davie, J. R., and Seto, E. (1997) J. Bio. Chem. 272, 28001–28007), etc. can be used. As known peptides which are known or expected to be deacetylated, for example, p53 (GU, W and Roeder, R. G. (1997) Cell 90 595–606), Histone (H1, H2A, $H_2B$, H3, H4) (Couppez, M., Ponthieu, A. M. and Sautiere, P. (1987) J. Bio. Chem. 262, 2854–2860, Hebbes, T. R., Thorne, A. W. and Robinson, C. C. (1988) EMBO J. 7, 1395–1402, Roth, S. Y. and Allis, C. D. (1996) Cell, 87, 5–8), TFIIE (Gu, W. and Roeder, R. G. (1997) Cell 90, 595–606), TFIIF (Gu, W., and Roeder, R. G. (1997) Cell 90, 595–606), PC4 (Gu, W. and Roeder, R. G. (1997) Cell 90, 595–606), etc., can be used.

Contacting a test peptide with an acetylated peptide substrate, and detecting an acetyl group on a peptide substrate can be done in the same manner as in the above method for detecting the acetyltransferase activity (a compound having acetyl group is not necessarily added to the reaction system of the contact reaction; refer to FIGS. 3 and 4). As a result, if a significant decrease of the acetyl group on a peptide substrate is detected, the test peptide is judged to have a deacetylase activity.

These systems for detecting the acetyltransferase and deacetylase activities can be used for screening inhibitors or enhancers of acetyltransferase and deacetylase. Therefore, the present invention relates to a method for screening a compound inhibiting or enhancing the activity of acetyltransferase and a method for screening a compound inhibiting the deacetylase activity.

The method for screening a compound inhibiting or enhancing the acetyltransferase activity of the present invention comprises the steps of: (a) contacting acetyltransferase with a peptide substrate in the presence of a test compound, (b) detecting an acetyl group binding to the peptide substrate using an anti-acetylated peptide antibody, and (c) screening a compound that decreases or increases the detected amount of the acetyl group binding to the peptide substrate, in comparison with the amount in the absence of the test compound (a control).

As a test compound used in this screening method, for example, a peptide (including proteins), a synthetic low-molecular-weight compound, a cellular extract or a cell culture supernatant derived from animals, plants, or microorganisms, etc., can be used, but is not restricted thereto. As an acetyltransferase, for example, GCN5 (Kuo, M.-H., Brownell, J. E. et al. (1996) Nature 383, 269–272; Brownell, J. E., and Allis, C. D. (1996) Curr. Opin. Genet. Dev. 6, 176–184; Candau, R., Zhou, JX., Allis, C. D. and Berger, S. L. (1997) EMBO J. 16, 555–565), P/CAF (Ogryzko, V. V., Sciltz, R. L., Russanova, V., Howard, B. H., and Nakatani, Y. (1996) Cell 87, 953–959), p300/CBP (Bannister, A. J., and Kouzarides. T. (1996) Nature 384, 641–643; Yang, X.-J., Ogryzko, V. V. et al. (1996) Nature 382, 319–382;Scolinick, D. M.,Chehab, N.H. and et al. (1997) Cancer Res. 57, 3693–3696; Gu, W., Shi, X.-L., and Roeder, R. G. (1997) Nature 387, 819–823; Lill, N. L., Grossman, S. R. et al. (1997) Nature 387, 823–827; Gu, W., and Roeder, R. G. (1997-) Cell 90, 595–606), TAFII250 (Mizzen, C. A., Yang, X.-Y. et al. (1996).Cell 87, 1261–1270), Tip60 (Kimura A., Yamamoto Y., and Horikosi M., Institute of Molecular and Cellular Biosciences, Laboratory of Developmental Biology, the University of Tokyo, Analysis of a novel histone acetyltransferase Tip60 family, presented at The Twentieth Annual Meeting of Japanese Association of Molecular Biology, Dec. 17, 1997), etc., and as a peptide substrate, for example, p53 (Gu, W. and Roeder, R. G. (1997) Cell 90, 595–606), histone (H1, H2A, $H_2B$, H3, H4) (Couppez, M., Ponthieu, A. M. and Sautiere, P. (1987) J. Bio. Chem. 262, 2854–2860; Hebbes, T. R., Throne, A. W. and Robinson, C. C. (1988) EMBO J. 7, 1395–1402; Roth, S. Y., and Allis, C. D. (1996) Cell 87, 5–8), TFIIE (Gu, W. and Roeder, R. G. (1997) Cell 90, 595–606), TFIIF (Gu, W. and Roeder, R. G. (1997) Cell 90, 595–606), PC4 Gu, W. and Roeder, R. G. (1997) Cell 90, 595–606) can be used, but is not restricted thereto.

Contacting a test peptide with a peptide substrate, and detecting an acetyl group on a peptide substrate can be done in the same manner as in the above method for detecting the acetyltransferase activity. As a result, if the detected amount of an acetyl group on a peptide substrate is significantly decreased in comparison with the amount in the absence of a test compound (a control), then the test compound used for screening is judged to inhibit the acetyltransferase activity. Conversely, an increase of the detected amount of an acetyl group that binds to a peptide substrate indicates that the test compound used for screening enhances acetyltransferase activity.

In the case of using a cellular extract, a cell culture supernatant from animals, plants, and microorganisms, and so on as a test compound, a single compound inhibiting or enhancing acetyltransferase activity can be finally identified by fractionating these through methods known to a person skilled in the art (for example, various kinds of chromatography) and detecting each of them.

The method for screening a compound that inhibits or enhances the deacetylase activity of the present invention comprises the steps of: (a) contacting deacetylase with an acetylated peptide substrate in the presence of a test compound; (b) detecting an acetyl group binding to the peptide substrate using an anti-acetylated peptide antibody; and, (c) screening a compound that decreases or increases the detected amount of the acetyl group binding to the peptide substrate in comparison with the amount in the absence of a test compound (a control).

As a test compound used in this screening method, for example, a peptide (including proteins), a synthetic low-molecular-weight compound, a cellular extract or a cell culture supernatant derived from animals, plants, and microorganisms, etc., but is not restricted thereto. As a deacetylase, for example, HrAC1/RPD3 (Taunton, J., Hassig, C. A., and Schreiber, S. L. (1996) Science 272, 408–411; Rundlett, S. E., Carmen, A. A., et al. (1996) Proc. Natl. Acad. Sci. USA 93, 14503–14508), HDAC2/YY-1BP (Yang, W.-M., Inouye, C., Zeng, Y. Y. Bearss, D., And Seto, E. (1996) Proc. Natl. Acad. Sci. USA 93, 12845–12850; Lusser, A., Brosch, G. et al. (1997) Science 277, 88–91), HDAC3 (Yang, W.-M., Yao, Y.-L., Sun, J.-M., Davie, J. R., and Seto, E. (1997) J. Bio. Chem. 272, 28001–28007) can be used. As a known peptide substrate, for example, p53 (Gu, W. and Roeder, R. G. (1997) Cell, 90 595–606), Histone (H1, H2A, $H_2B$, H3, H4) (Couppez, M., Ponthieu, A. M. and Sautiere, P. (1987) J. Bio. Chem. 262, 2854–2860; Hebbes, T. R., Thorne, A. W. and Robinson, C. C. (1988) EMBO J. 7, 1395–1402; Roth, S. Y. and Allis, C. D. (1996) Cell, 87, 5–8), TFIIE (Gu, W. and Roeder, R. G. (1997) Cell 90, 595–606), TFIIF (Gu, W., and Roeder, R. G. (1997) Cell 90, 595–606), PC4 (Gu, W. and Roeder, R. G. (1997) Cell 90, 595–606), etc, can be used, but not restricted thereto.

Contacting a test peptide with an acetylated peptide substrate, and detecting an acetyl group on a peptide substrate can be done in the same manner as in the above method for detecting the deacetylase activity. As a result, if the detected amount of the acetyl group binding to a peptide substrate is increased in comparison with the amount in the absence of the test compound (control), then the test compound used for screening is judged to inhibit the deacetylase activity. On the other hand, if the detected amount of acetyl group binding to a peptide substrate is lowered, the test compound used for screening is judged to enhance deacetylase activity. When a cellular extract or a cell culture supernatant of animals, plants and microorganisms, and such are used as a test compound, these can be fractionated using methods known to a person skilled in the art (for example, various kinds of chromatography) and detected to identify a single compound inhibiting the deacetylase activity.

A compound that inhibits or enhances the acetyltransferase and deacetylase activities, isolated by these screenings is useful as a drug-candidate compound for cancer treatment or as anti-fungal antibiotics.

As to the detection of acetylation and deacetylation in a peptide substrate, not only acetylation and deacetylation by enzymes, but also non-enzymatic acetylation and deacetylation have been reported. For example, cyclooxygenase is an incipient enzyme which synthesizes prostaglandin and thromboxane from arachidonic acid, and it has been reported that acetylation of the $530^{th}$ serine residue located close to the activation site of cyclooxygenase by aspirin, inhibits enzyme reaction (reference: Patrono, C. et al. (1989) *Trend. Pharmacol. Sci.* 10, 453–458). Therefore, the detection method of the present invention can be used not only for detecting the acetyltransferase and deacetylase activities in a protein, but also, for detecting the acetylation and deacetylation activities in various compounds including a synthetic low-molecular-weight compound, etc. Moreover, a compound which inhibits or enhances acetylation and deacetylation activities in these compounds can also be screened.

The present invention also relates to a method for screening a compound inhibiting the activity of deacetylase or a compound enhancing the activity or expression of acetyltransferase, using cultured cells. In one embodiment of this screening method, an anti-acetylated peptide antibody is used and, comprising the steps of: (a) contacting a test compound with cultured cells; (b) immobilizing said cultured cells; (c) detecting an acetyl group on a specific protein in said cultured cells using an anti-acetylated peptide antibody; and, (d) screening a compound that increases the acetyl group on said specific protein in comparison with a control untreated with the test compound.

In this screening, any protein that can be acetylated in cultured cells can be used as a protein subjected to the detection of an acetyl group. For example, histone, TFIIEβ, TFIIF, p53, EKLF, GATA-1, HMG1 (Y), and such, can be used.

As a test compound used, for example a peptide (including a protein), a synthetic low-molecular-weight compound, a cellular extract or a cell culture supernatant of animals plants or microorganisms, can be used, but is not restricted thereto.

As cultured cells brought with a test compound, any cells capable of being cultured can be used, but adhesive cells are preferred for convenience of handling. Examples are, HEp-G, HEp-2, Hela, etc., can be used. These are easily publicly acquirable and can be cultured under the conditions described in the respective brochures, etc.

Cells can be immobilized by methods known to a person skilled in the art, and, for example, methanol, acetone, paraformaldehyde, and such, can be used.

An anti-acetylated peptide antibody used for detecting acetyl group on a protein can be monoclonal or polyclonal antibodies. These antibodies can be prepared by methods known to a person skilled in the art (refer to, for example, Cell Engineering, Supplement, Protocol for Anti-Peptide Antibody Experiment, 1994, Shujun-Sha, Turner, B. M. and Fellows, G, (1989) Eur. J. Biochem. 179, 131–139; Muller, S., Isabey, A. et al. (1987) Molecular Immunology 24, 779–789; Pfeffer, U., Ferrari, N. and Vidali, G. (1986) J Bio. Chem. 261, 2496–2498). An anti-acetylated peptide antibody is appropriately labeled for the detection of an acetyl group in a protein. Any label with a detectable sensitivity, for example, an enzyme label, such as peroxidase, β-D-galactosidase, alkaline phosphatase, glucose-6-phosphate dehydrogenase, acetylcholinesterase, etc., a fluorescent label, such as delphinium, etc., and a radioactive label, etc., can be used as a label. Detection can be done by labeling a substance specifically binding to an anti-acetylated peptide antibody, for example, second antibody, protein A, protein G, protein A/G (a fused protein of A and G), etc., without labeling an anti-acetylated peptide antibody.

As a result of detecting an acetyl group on a protein, if a significant increase of the detected amount of acetyl group in the groups treated with a test compound is detected in comparison with a control untreated with the test compound, then the test compound can be a candidate for a compound that inhibits the activity of deacetylase, or enhances activity or expression of acetyltransferase.

Another embodiment of the methods for screening a compound which inhibits the activity of deacetylase, or a compound which enhances activity or expression of acetyltransferase by using cultured cells of the present invention, relates to the method of using promoter and reporter genes functioning in cultured cells.

In the present example described below, an expression vector for mammalian cells, ligated to the GEP gene, was introduced into a cell, and a cell into which the vector was stably introduced was selected by treatment with a reagent. Significant difference in the expression of GFP was observed among the cells. The treatment of the cells in which the expression of GFP was low with inhibitors of histone deacetylase, increased luminescence intensity of GFP in these cells.

This fact demonstrates that inhibition of said promoter is released by treating the cells with a deacetylase inhibitor and the expression of GFP downstream of the promoter has been induced, suggesting that the promoter is inhibited by the deacetylation of histone.

Based on this knowledge, a compound which inhibits the deacetylase activity of histone or a compound which enhances activity or expression of acetyltransferase activity of histone can be screened by preparing a cell introduced with a vector, in which a reporter gene is ligated to the downstream of a promoter functioning in the cultured cell, treating said cells with a test compound, and then detecting the induction of the reporter gene expression.

Specifically, the screening method of the present invention comprises the steps of: (a) providing cultured cells carrying a vector in which a promoter that functions within cultured cells and a reporter gene ligated to the downstream of said promoter, (b) contacting a test compound with said cultured cells, and, (c) screening a compound that increases the reporter activity, in comparison with a control untreated with a test compound.

For example, a peptide (including proteins), a synthetic low-molecular-weight compound, a cellular extract or a supernatant of cell culture of animals, plants, or microorganisms, etc., can be used as a test compound used for this screening, but is not restricted thereto.

Any cells derived from mammals can be used as cultured cells, however, adhesive cells are preferable due to the convenience of handling. Examples of such cells are HEp-G, HEp-2, and Hela, etc. These cells are readily available and can be cultured under the culture conditions described in the manufacturer's respective brochure.

As a promoter contained in a vector, for example, a virus-derived promoter used as a general expression vector can be utilized. As a reporter gene, luciferase gene, chloramphenicol acetyltransferase (CAT) gene, growth hormone gene, can be used besides GFP. A vector used in the present invention preferably contains a selection marker gene, namely, a gene for selecting cells into which said vector is introduced. General gene manipulations such as insertion of a promoter and such, and introduction of a reporter gene into a vector can be performed by methods known to a person skilled in the art.

A method for selecting cells into which a vector is introduced depends on the selection marker inserted into the vector. For example, in the case of using a neomycin resistance gene as the reporter gene, transformant cells can be screened by culturing the cells in a medium containing neomycin because only those cells into which the neomycin resistance gene (neo) is introduced and expressed can grow.

In the screening method of the present invention, among the screened transformant cells (cells into which a vector is introduced), further screening of cells in which the transcriptional activity by a promoter is inhibited are done by, observations using a florescent microscope, Western blotting using an antibody against a translational product of the reporter gene, or amplification of the reporter gene by PCR. The screening of a target compound using said cells is preferable as it improves the efficiency of screening.

A method for detecting the reporter activity in cultured cells depends on the kind of reporter gene. For example, in the case of GFP, a cell expressing this protein is exposed to ultraviolet light to emit florescence, thus the presence or absence of the expression of the gene can be visually detected by this coloring reaction.

As a result of the detection, in comparison with a control untreated with a test compound, if there is significant increase of the reporter activity in the group treated with the test compound, the used test compound can be a candidate for a compound that inhibits the activity of deacetylase or enhances the activity or expression of acetyltransferase.

Moreover, the present invention relates to a kit comprising an anti-acetylated peptide antibody used for detecting the above acetyltransferase activity or deacetylase activity and screening of a compound which inhibits or enhances the activities of these enzymes. The kit of the present invention may contain, for example, acetyltransferase, a peptide substrate, and/or buffer, besides an anti-acetylated peptide antibody when used for detecting acetyltransferase activity. When the kit is used for detecting the deacetylase activity, it may contain deacetylase, an acetylated peptide substrate, and/or buffer besides an anti-acetylated peptide antibody.

The kit of the present invention may further contain a test compound besides those described above when used for screening a compound which inhibits or enhances acetyltransferase or deacetylase activities by using the system for detecting activities of these enzymes. The peptide substrate and the anti-acetylated peptide antibody may be labeled by the above labels. An enzyme standard, a peptide substrate standard and an anti-acetylated peptide antibody standard may contain other components in order to stabilize proteins, etc. For example, the addition of about 1% BSA and polyols, such as sucrose and fructose, etc., with a final concentration of 0.2 to 10% (preferably 1%) to the standard is preferable for preventing the denaturation of the protein after freeze-drying. As a buffer for detecting acetyltransferase activity or for screening inhibitors or enhancers of said enzyme, for example, "50 mM Tris-HCl pH8.0, 10% glycerol, 1 mM DTT, 1 mM PMSF, 10 mM sodium butyrate, 200 nM acetyl-COA", described in Examples can be used. As a buffer for detecting the deacetylase activity or for screening inhibitors or enhancers of said enzyme, for example, "10 mM Tris-HCl pH 8.0, 10 mM EDTA, 150 mM NaCl" used in the examples described below can be used.

When cultured cells are used for the screening of the present invention, the kit of the present invention may contain a test compound and/or a buffer besides an anti-acetylated peptide antibody.

BEST MODE FOR CARRYING OUT THE INVENTION

Figure 1:
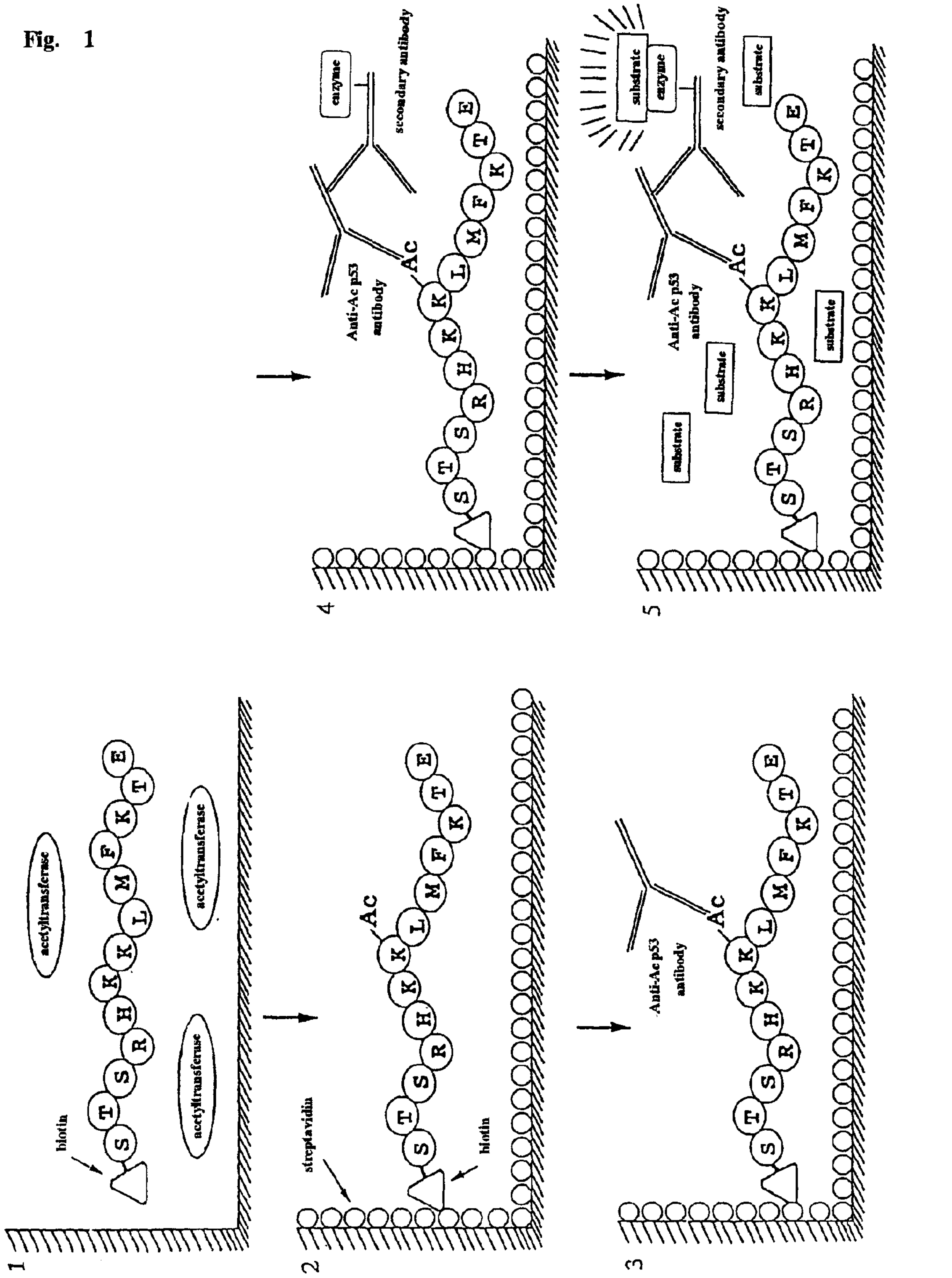
FIG. 1 shows the procedure (one example) of the liquid phase analysis system for acetyltransferase activity using an anti-acetylated peptide antibody.

The present invention is illustrated in detail with examples below, but is not to be construed being restricted thereto.

EXAMPLE 1

Preparation of an Anti-Acetylated Peptide Antibody

1. Preparation of an Immunogen (1) Preparation of a Peptide

Four peptides comprising the 373rd and 382nd lysine residues of human p53, reported as acetylation sites were prepared by a peptide synthesizer. These peptides are "Ac p53-1" (SEQ ID NO: 1/STSRHKK (Ac) LMFKTEC), "p53-1" (SEQ ID NO: 2/STSRHKKLMFKTEC), "AC p53-2" (SEQ ID NO: 3/SHLKSKK (Ac) GQSTSRC) and "p53-2" (SEQ ID NO: 4/SHLKSKKGQSTSRC). Amino acids are given in one-letter codes, and K(AC) indicates an acetylated lysine residue. HPLC confirmed that the purity of synthesized peptides was 90% or more. "Ac p53-1" and "p53-1" are composed of amino acids residues 367 to 388 of human p53, "Ac p53-2" and "p53-2" are composed of amino acid residues 367 to 379 of human p53. The cysteine residue at the carboxyl terminus in all peptides was inserted for binding a peptide into a carrier protein.

(2) Binding a peptide into a carrier protein

Each acetylated peptide ("Ac p53-1" and "Ac p53-2") was covalently bound to keyhole limpet hemocyanin (KLH), a carrier protein, to prepare an immunogen. m-Maleimidebenzoyl-N-hydroxysuccinimide ester (MBS) was used as a cross-linking agent for binding between the peptide and KLH. Equal amounts of KLH and peptides were cross-linked. This peptide-KLH was used as an immunogen.

2. Immunization and Collection of Blood (1) The method for Immunization and Confirmation of Antibody Titer 200 μg (100 μl) of a carrier protein KLH and the peptide binding thereto (peptide-KLH) were used as an immunogen for a single-immunization of a rabbit. Equal amounts of Freund's complete adjuvant and peptide-KLH (100 μl each) were completely emulsified in a 1.5-ml tube using a 1-ml syringe with a 21-gudge injection needle. This emulsion of peptide-KLH and adjuvant was subcutaneously injected into 4 to 5 sites in the back of the rabbits (Japanese white) with a 26-gauge injection needle once every week, five times in total (immunization). At the fifth immunization, several milliliters of blood was collected from the ear-lobe vein to confirm the antibody titer by the ELISA method.

(2) Collection of blood

From one week after confirmation of a sufficient titer, one 3-week cycle composed of blood collection (first week), rest (second week), and immunization (third week) was repeated four times. Blood was collected from the ear-lobe vein in the same manner as in the confirmation of antibody titer. About 60 to 70 ml of blood was collected per each collection. At the fifth collection, blood was collected as much as possible from the heart with a catheter.

(3) Collection and storage of serum and separation of antibody fraction.

The collected blood was placed at 4° C. overnight to coagulate and serum was separated. Sodium azide was added to the separated and collected serum to a final concentration of 0.1%, and was stored at 4° C. Ammonium sulfate was added to the collected serum to a final concentration of 50% to separate and concentrate the antibody fraction, and stirred for one hour or longer at 30° C. The precipitate was collected by supercentrifugation. The precipitate was dissolved with a minimum amount of pure water and dialyzed against PBS using a permeable membrane. After completely equilibrating to PBS, this antibody fraction was loaded onto a column to purify the antibody.

3. Preparation of a Specific Antibody (1) Preparation of a Specific Column and an Absorption Column A peptide was bound to Sepharose 4B by mixing 1 to 2 g of an CNBr-activated Sepharose 4B and 1 mg of peptide in 5 to 10 ml of 0.1 M carbonate buffer overnight at 4° C. by using a rotator. On the following day, Sepharose 4B was packed into the column, and washed with PBS 4 to 10 folds of the column volume. The column was equilibrated with 1M Tris-HCl (pH 7.0) and left at 30° C. for one hour or longer to block the residual active groups on the surface of Sepharose 4B. After blocking, the column was washed and equilibrated with PBS and used.

(2) Preparation of an anti-acetylated peptide antibody by specific and absorption columns For preparing an anti-acetylated peptide specific antibody, anti-"Ac p53-1", and anti- "Ac p53-2" antibody fractions were passed through each specific column. After the column was washed with PBS-0.1% Tween 20, the anti-acetylated peptide antibody absorbed on the column was eluted with 0.1 M glycine-HCl (pH 3.0). The antibody fraction eluted from the specific column was passed through an absorption column. Anti- "Ac p53-1" antibody fraction and anti-"Ac p53-2" antibody fraction were passed through a "p53-1" Sepharose 4B column, and a "p53-2" Sepharose 4B column, respectively. By passing through these columns, antibodies which react not only specifically to acetylated peptides but also to non-acetylated peptides were absorbed on each column. The anti-acetylated peptide specific antibody does not get absorbed on the column and passes through the column. After each antibody fraction was passed, the absorption column was washed with PBS-0.1% Tween 20, and anti-non-acetylated peptide antibodies were eluted with 0.1 M glycine-HCl (pH 3.0). After elution, the column was equilibrated with PBS-0.1% Tween 20 again. The antibody fraction was passed through the absorption column several times until non-acetylated peptide antibodies were completely absorbed. The progression of absorption was confirmed by ELISA using a non-acetylated peptide sensitized plate. The anti-"Ac p53-1" antibody fraction and the anti-NAc p53-2" antibody fraction from which the anti-non-acetylated peptide antibodies were removed completely by being absorbed by the absorption column were passed through the "Ac p53-2" Sepharose 4B column and the "Ac p53-1" Sepharose 4B column, respectively. An acetylated lysine residue specific antibody considered to be contained in the antibody fraction was absorbed through this treatment. The progression of this absorption was confirmed by ELISA using a acetylated peptide sensitized plate. The antibody (an anti-acetylated peptide specific antibody) that was completely absorbed in the absorption column was dialyzed against PBS, and the specificity against the acetylated peptide was ultimately confirmed by ELISA using an acetylated peptide sensitized plate.

(3) Preparation and use of the ELISA Plate for Detecting Antibody Titer and Specificity of Antibody A peptide was dissolved in PBS to a final concentration of 10 μg/ml, and 50 μl thereof was seeded to each well of a microtiter plate for ELISA, and sensitized overnight at 4° C. After sensitization, the peptide solution was removed and 200 μl of 1% BSA-0.1% Tween 20-PBS was added to each well and blocking was performed for one hour or longer at 30° C. The acetylated peptide ("Ac p53-1" and "Ac p53-2") sensitized plates were used for measuring antibody titer, absorbing an anti-acetylated lysine residue specific antibody, and confirming the specificity of the anti-acetylated peptide antibody. The non-acetylated peptide ("p53-1", and "p53-2") sensitized plate was used for confirming the absorption of a non-specific antibody by a column. Serum and antibody were diluted with 0.1% Tween 20-PBS according to needs. Each diluted sample (100 μl) was added to each well of the sensitized plate and left at 30° C. for 1 hour (the first reaction). After the first reaction, each well was washed enough with 0.1% Tween 20-PBS four times using a washing bottle. Goat anti-rabbit IgG (H+L) horse radish peroxidase labeled antibody (MBL 458) diluted to 3000 folds with 0.1% Tween 20-PBS (100 μl) was added to each well and left at 30° C. for 1 hour (the second reaction). After the second reaction, the plate was washed with 0.1% Tween 20-PBS in the same manner, 750 μM tetramethyl benzidine (TMB) (100 μl) was added to each well, and incubated for 5 to 20 min at 30° C. (the coloring reaction). 100 μl of 1.5 N phosphate buffer was added to terminate the coloring reaction and absorbance at 450 nm was measured by a microtiter plate reader.

(4) Confirmation of Specificity

Figure 5:
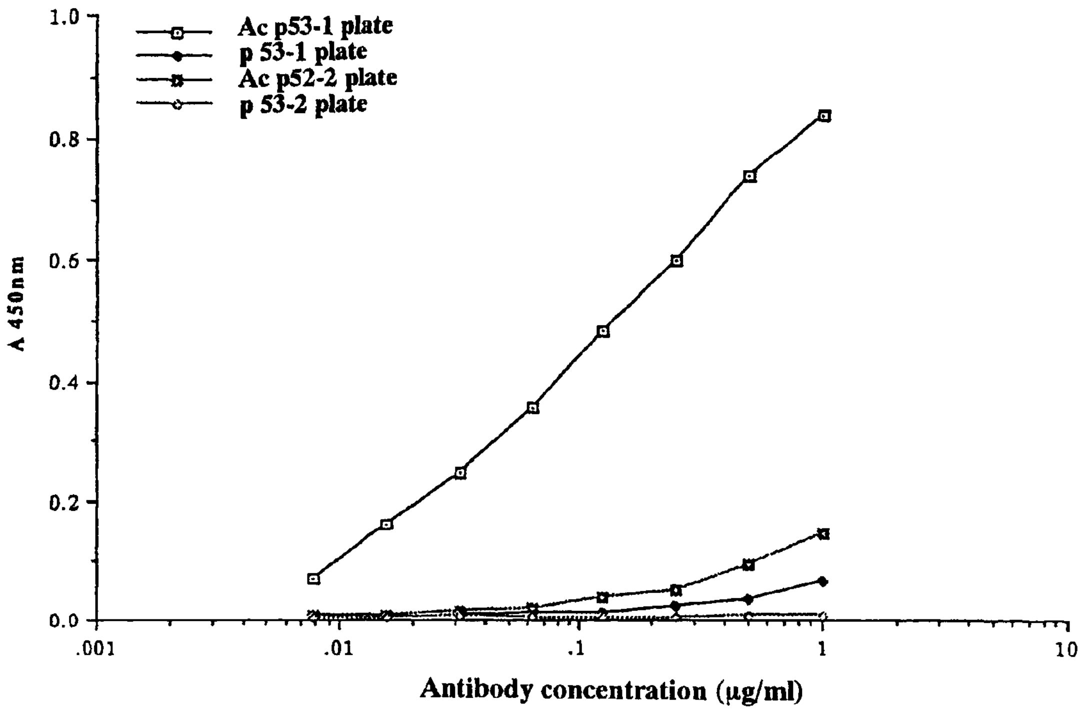
FIG. 5 shows the specificity of the anti-Ac p53-1 antibody.
Figure 6:
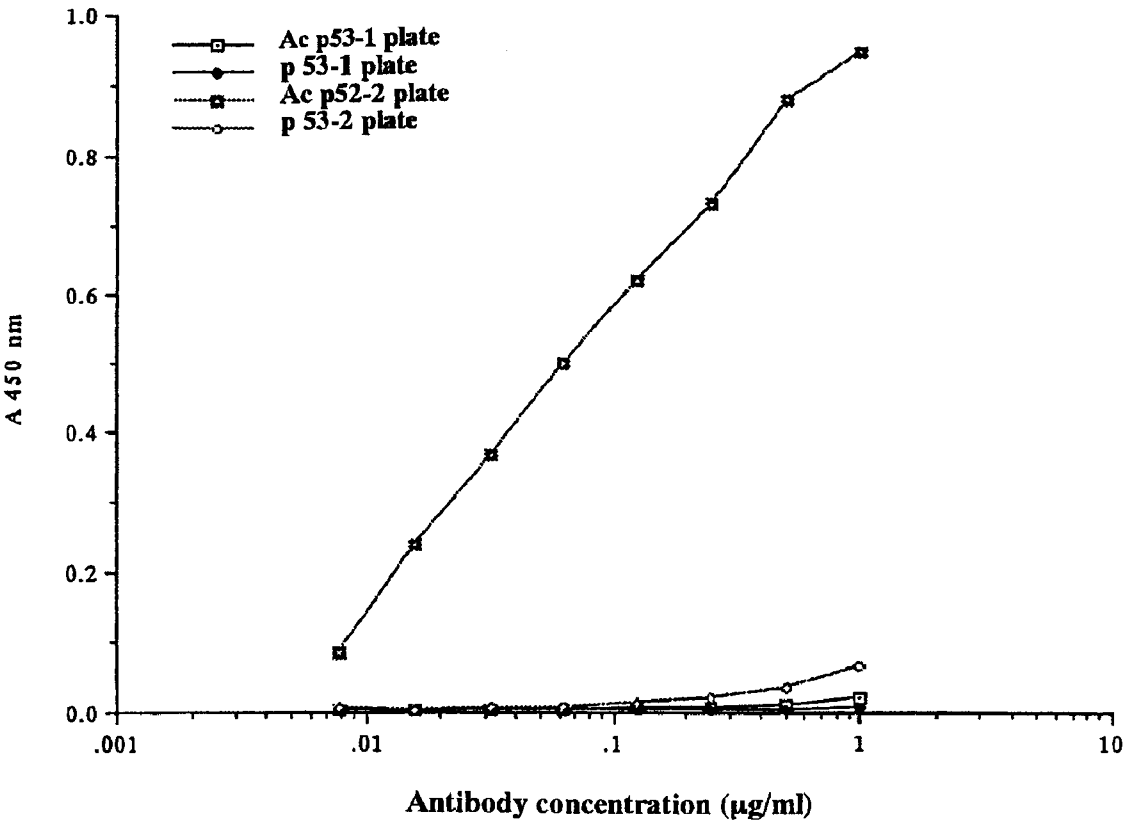
FIG. 6 shows the specificity of the anti-Ac p53-2 antibody.
Figure 7:
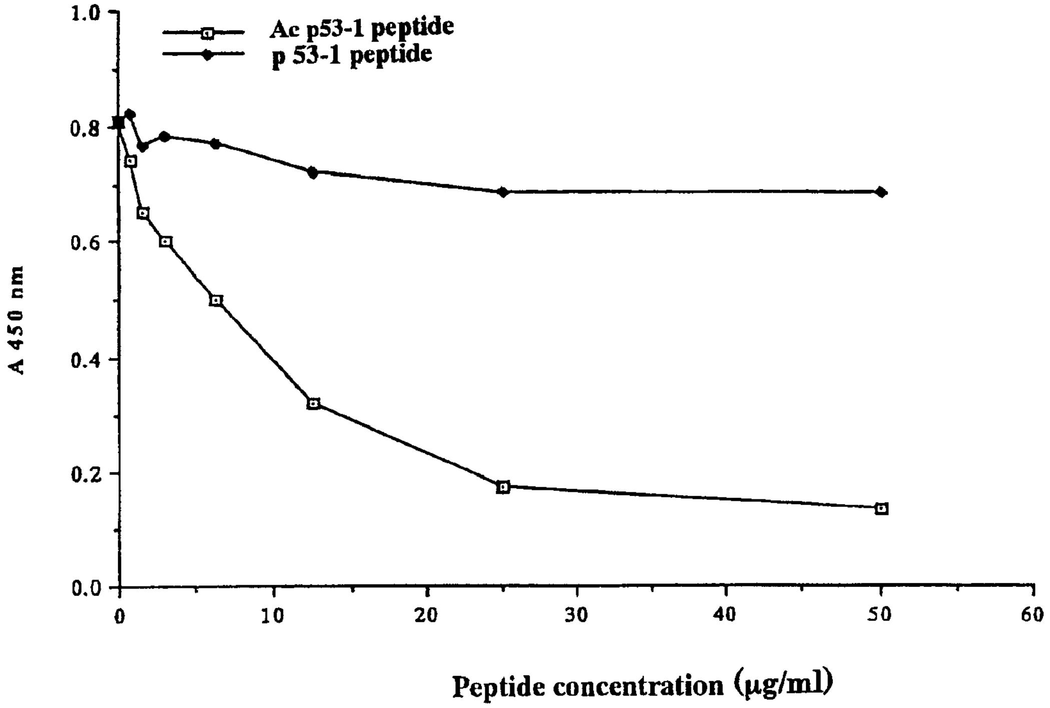
FIG. 7 shows the result of the competitive inhibition analysis of the anti-Ac p53-1 antibody.
Figure 8:
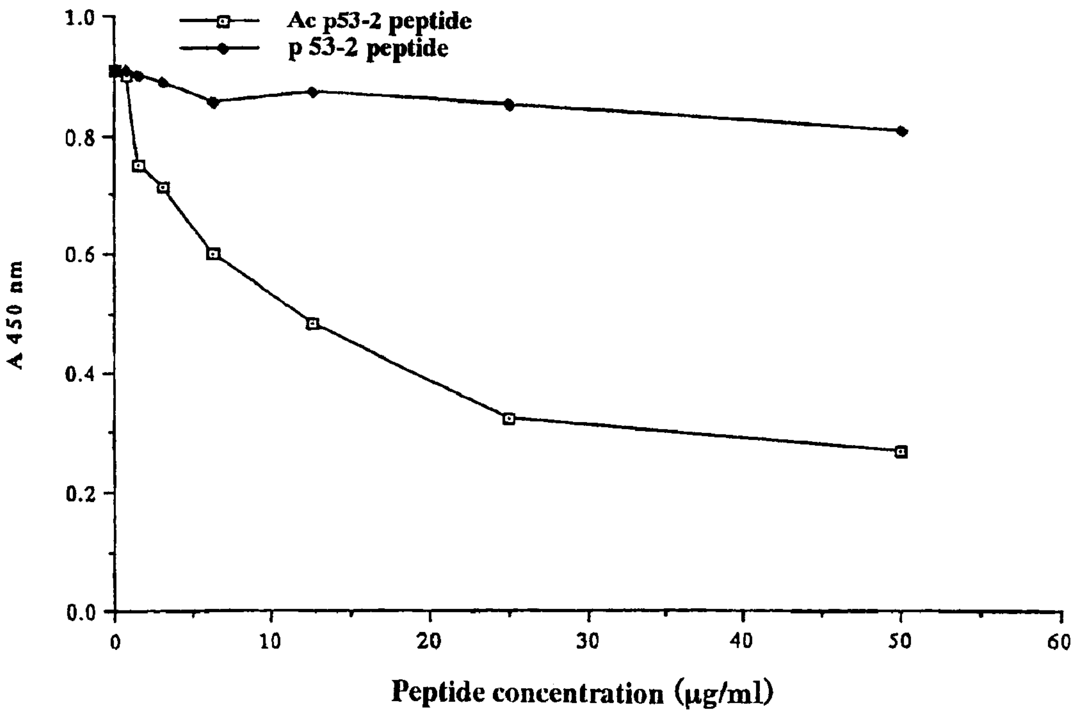
FIG. 8 shows the result of the competitive inhibition analysis of an anti-Ac p53-2 antibody.

The anti- "Ac p53-1" specific antibody and the anti- "Ac p53-2" specific antibody were diluted to 0.01 to 1.0 μg/ml and specificity of each was determined by a respective peptide sensitized plate (FIGS. 5 and 6). As a result, the reaction of each antibody against the respective acetylated peptide was observed, however, the reaction to the other acetylated peptide or a non-acetylated peptide was hardly observed. The antibody diluted into 0.5 μg/ml was added at 0 to 50 μg/ml to each acetylated peptide and non-acetylated peptide and bound at room temperature for 1 hour. Competitive inhibition test was conducted using each acetylated peptide sensitized plate (FIGS. 7 and 8). As a result, the reaction of the antibodies was specifically inhibited by each acetylated peptide. From the above results, the purified antibodies were confirmed to have specificities only to the acetylated peptide.

EXAMPLE 2

Preparation of Acetyltransferase and Deacetylase by Genetic Engineering

1. Isolation of Genes by PCR (1) Acetyltransferase

Up to now, as acetyltransferases of p53 and mammalian histone, five genes: P300/CBP, Gcn5, TAFII250, P/CAF, and Tip 60 have been reported. Among them, P300 and CBP are different genes, however, their nucleotide and amino acid sequences are highly homologous. Among these acetyltransferases, P300/CBP and Gcn5 were amplified and isolated by PCR method. The following PCR primers were prepared. For amplifying P300/CBP, a forward primer "CBPF" [SEQ ID NO: 5/5'-GCGGGATCCCAGAA-TAGGTATCATTTCTGTGAG-3' [the three nucleotides (GCG) at the 5' end were added for enhancing the treatment with restriction enzymes, and forth to ninth nucleotides (GGATCC) from the 5' end is the restriction enzyme BamHI site] and a reverse primer "CBPR" [SEQ ID NO: 6/5'-AGACTCGAGCTTGCACTCGTTGCAGGTGTAGAC-3' (the three nucleotides (AGA) at the 5' end were added for enhancing the treatment with restriction enzymes, and forth to ninth nucleotides (CTCGAG) from the 5' end is the restriction enzyme XhoI site) were used. By using this primer set, the DNAs coding amino acids 1195 to 1673 of P300 and those 1231 to 1710 of CBP, reported as the acetyltransferase activation sites, were amplified by PCR. For amplifying Gcn5, a forward primer "Gcn5F" [SEQ ID NO: 7/5'-TATGGATCCATGCTGGAGGAGGA-GATCTATG-3' (the three nucleotides (TAT) at the 5' end were added for enhancing the treatment with restriction enzymes, and forth to ninth nucleotides (GGATCC) from the 5' end is the restriction enzyme BamHI site) and a reverse primer "Gcn5R" [SEQ ID NO: 8/5'-TATCTCGAG-CTTGTCAATGAGGCCTCCCTCC-3' (the three nucleotides (TAT) at the 5' end were added for enhancing the treatment with restriction enzymes, and forth to ninth nuceltides (CTCGAG) at the 5' end is the restriction enzyme XhoI site) were used. By using this primer set, the DNA encoding amino acids 1 to 476 of Gcn5 (the full length) was amplified by PCR.

(2) Deacetylase Gene

Up to now, three deacetylation genes: HDAC1/RPD3, HDAC2/YY-1BP and HDAC3, have been reported. Among these deacetylase genes, HDAC1/RPD3 and HDAC3 were amplified and isolated by PCR method. The following PCR primers were prepared. For amplifying HDAC1/RPD3, a forward primer "HD1F" [SEQ ID NO: 9/5'-CGCGGATCCATGGCGCAGACGCAGGGCACC-3' (the three nucleotides (CGC) at 5' were added for enhancing the treatment with restriction enzymes, and forth to ninth (GGATCC) at 5' is the restriction enzyme BamHI site) and a reverse primer "HD1R" [SEQ ID NO: 10/5'-CGCCTCGAGGGCCAACTTGACCTCCTCCTT-3' (the three nucleotides (CGC) at the 5' end were added for enhancing the treatment with restriction enzymes, and forth to ninth nucleotides (CTCGAG) at the 5' end is the restriction enzyme XhoI site) were used. By using this primer set, the DNA encoding amino acids 1 to 482 of HDAC1/RPD3 (the full length) was amplified. For amplifying HDAC3, a forward primer "HD3F" [SEQ ID NO: 11/5'-CGCGGATCCATGGCCAAGACCGTGGCGTAT-3' (the three nucleotides (CGC) at the 5' end were added for enhancing the treatment with restriction enzymes, and forth to ninth nucleotides (GGATCC) from the 5' end is the restriction enzyme BamHI site) and a reverse primer "HD3R" [SEQ ID NO: 12/5'-CGCCTCGAGAA-TCTCCACATCGCTTTCCTT-3' (the three nucleotides (CGC) at the 5' end were added for enhancing the treatment with restriction enzymes, and forth to ninth nucleotides (CTCGAG) from the 5' end is the restriction enzyme XhoI site) were used. By using this primer set, the DNA encoding amino acids 1 to 428 of HDAC3 (the full length) was amplified.

(3) Conditions for PCR

As a template for amplifying the acetyltransferase and deacetylase genes by PCR, cDNA of human uterocervical cancer derived HeLa cells was used. For preparing cDNA, total RNA was extracted from HeLa cells by using the phenol-thiocyanate guanidine method (Nippon Gene, ISOGEN) and purified. From the extracted total RNA, cDNA was synthesized using random primers (reverse transcription reaction). PCR reaction was conducted basically under the condition of 1) 1 cycle at 92° C. for 3 min, 2) 35 cycles at 92° C. for 1 min (denaturation), at the temperature described below for 1 min (annealing), and at 72° C. for 1 min (extension) and 3) one or more cycles at 72° C. for 10 min.

Annealing temperature varied depending on the primer set for each gene. Specifically, for the primer set "CBPF-CBPR" it was 55° C., for that of "Gcn5F-Gcn5R" was 66° C., for that of "HD1F-HD1R" was 64° C., and for that of "HD3F-HD3R" was 64° C. Taq polymerase was used as a resistant DNA polymerase for PCR.

2. Subcloning of the PCR products into an expression vector (1) Purification of the PCR Products Each DNA band (a PCR product) amplified by PCR was confirmed by 1% agarose gel electrophoresis. After confirmation of the bands, each PCR product was treated with restriction enzymes BamHI and XhoI. By this treatment, the restriction enzyme site inserted at 5' end in each PCR primer was cleaved to generate adhesive ends at both sides of the PCR products. Each PCR product treated with restriction enzymes was separated by the agarose gel electrophoresis. The bands of PCR products separated by the agarose gel was excised together with gel, separated and purified from the agarose by glass milk.

(2) Ligation into an Expression Vector

The PCR products separated and purified from the agarose gel was subcloned into the cloning site of expression vectors PGEX and pET. The expression vectors were treated in advance with the restriction enzymes BamHI and XhoI same as those used at the ends of PCR products and separated and purified with the agarose gel. The PCR products and expression vectors were mixed to equivalent molar concentrations and ligated with T4 ligase. Ligation was conducted at 16° C. for 1 hour.

(3) Transformation of *E. coli*

After ligation, each sample was inserted into competent *E. coli* DH5a made by the rubidium chloride method (transformation). Competent DH5 α (100 μl) and each ligated sample (101) were gently mixed in a 1.5-ml tube and placed on ice for 30 min. The tube was quickly transferred to warm water at 42° C., heat-shocked for 30 sec, returned onto ice, and allowed to stand there for several min. SOC. medium (1.0 ml) was added to each tube and left-aside for 1 hour at 37° C. These were spread on a LB plate containing 50 μg/ml ampicillin which is an antibiotic for selecting expression vectors pGEX and pET. These plates were cultured at 37° C. overnight.

3. Purification of a recombinant protein from *E. coli*

(1) Confirmation of an Insert and its Sequence

Several colonies were picked up from the plates, and cultured in a LB-ampicillin medium overnight. Plasmids (the expression vector) were purified from the cultured *E. coli* by the alkaline method. The se plasmids were treated with the restriction enzymes BamHI and XhoI and an insert (the PCR product) was confirmed by the agarose gel electrophoresis. The nucleotide sequences of the inserts in these plasmids were confirmed based on the Sanger method using an automatic sequencer.

(2) Expression of the Recombinant Proteins in pGEX Vector and Purification

*E. coli* (DHα5) having the correct plasmid was incubated in the LB-ampicillin medium overnight. A part of the culture medium incubated overnight was added to the LB-ampicillin medium to dilute into several ten-folds. The medium was cultured while shaking at 37° C. for several hours, periodically measuring the turbidity of the medium at 600 nm. When turbidity reached to 0.6 to 1.0, IPTG was added to the culture medium to a final concentration of 1 mM for inducing expression of the recombinant proteins, and further cultured for 4 hours. Bacterial cells were harvested from the culture medium by centrifugation. A part of the collected bacterial cells was subjected to SDS-polyacrylamide gel electrophoresis (SDS-PAGE). After electrophoresis, the gel was stained with Coomassie Blue to confirm the bands of the recombinant proteins whose expression was induced. In PGEX vector, the recombinant protein is constructed as a fused protein with glutathione-s-transferase (GST). Using the extremely high affinity of this reduced GST against glutathione, the recombinant proteins were purified. After the expression of the recombinant proteins was confirmed, the bacterial cells were well suspended in 1% Tween 20-PBS and disrupted by sonication. The soluble fraction containing the recombinant proteins was collected by supercentrifugation. This soluble fraction was passed through a GSH-Sepharose 4B column, and the recombinant protein fused with GST was absorbed onto the column. The column was washed well with WE buffer (10 mM 2-mercaptoethanol, 2 mM $MgCl_2$, 20 mM Tris-HCl at pH 7.5) and the recombinant proteins were eluted using G buffer (10 mM GSH, 50 mM Tris-HCl pH 9.6).

(3) Expression of the Recombinant Proteins in pET Vector and Purification

The expression of the recombinant proteins in pET vector is induced by T7 RNA polymerase. Therefore, the expression plasmid was used to transform *E. coli* BL21 (DE3) having the T7 RNA polymerase gene. T7 RNA polymerase in BL21 (DE3) is induced by IPTG, thus the expression of the recombinant proteins was induced by adding IPTG to the medium in the same manner as for pGEX vector. After the induction, in the same manner as for pGEX, bacterial cells were harvested from the culture medium by centrifugation, and a part of the bacterial cells were subjected to the SDS-polyacrylamide gel electrophoresis (SDS-PAGE). After electrophoresis, the gel was stained with Coomassie Blue to confirm the bands of the recombinant proteins whose expression was induced. In pET vector, six successive histidines (6His-Tag) were added to both ends of the recombinant proteins. The recombinant proteins were purified using the property that this 6His-Tag forms a complex with nickel. After the expression of the recombinant proteins was confirmed, the bacterial cells were suspended well in the binding buffer (5 mM imidazole, 0.5 M NaCl, 20 mM Tris-HCl pH 7.0, 0.1% NP-40), and disrupted by sonication. The soluble fraction containing the recombinant proteins was collected from the supernatant by supercentrifugation. This soluble fraction was loaded onto a Ni-NTA-agarose column and the recombinant proteins were absorbed on the column through 6His-Tag. The column was washed well with the binding buffer and further washed with the washing buffer (10 mM imidazole, 0.5 M NaCl, 20 mM Tris-HCl pH 7.9). The recombinant proteins were eluted with the elution buffer (50 mM to 1 M imidazole, 0.5 M NaCl, 20 mM Tris-HCl pH 7.9) (the concentration of imidazole was gradually increased from 50 mM, 100 mM, 200 mM, to 1 M).

EXAMPLE 3

System for Measuring the Acetyltransferase Activity

1. Construction of an ELISA system for measuring the acetyltransferase activity (1) Construction of a Peptide Substrate and Recombinant p53-C ter Protein Two peptide substrates "Sub p53-1" (SEQ ID NO: 13/Bio-STSRHKKLMFKTE) and "Sub p53-2" (SEQ ID NO: 14/Bio-SHLKSKKGQSTSR) comprising the 373rd and 382nd lysine residues of the amino acid sequence of human p53, respectively, reported as an acetylation sites of acetyltransferase, were prepared by a peptide synthesizer. Amino acids in the peptide are shown in one-letter codes, and "Bio" at the amino ends means biotin. Ninety percent or higher purity was confirmed by HPLC. "Sub p53-1" and "Sub-p53-2" were composed of amino acids 376 to 388 and amino acids 367 to 379, respectively. The DNA comprising the genetic information of 110 amino acids (residues 284 to 393) at the carboxyl end in p53 was amplified using the primer set "p53cF" [SEQ ID NO: 15/5'-TATGGATCCACAGAGGAAGAGAATCTCCGC-3' [the three nucleotides (TAT) at the 5' end are for enhancing the treatment with restriction enzymes. The 4th to 9th nucleotides (GGATCC) from the 5' end produce the restriction enzyme BamHI site] and "p53cR" [SEQ ID NO: 16/5'-TATCTCGAGGTCTGAGTCAGGCCCTTCTGA-3' [the three nucleotides (TAT) at the 5' end are for enhancing the treatment with restriction enzymes. The 4th to 9th nucleotides (CTCGAG) from the 5' end produce the restriction enzyme XhoI site] by PCR method. The amplified PCR product was subcloned to pGEX, expressed as a fusion with GST, and purified (GST-p53 Cter).

(2) Preparation of a Peptide Substrate, "GST-p53 Cter" and a Streptoavidin Sensitized Plate Two peptide substrates were dissolved in PBS to 10 μg/ml. The peptide solution (50 μl) was seeded into each well of amicrotiter plate for ELISA, and sensitized at 4° C. overnight. After sensitization, the peptide solution was removed and 200 μl of 1% BSA-0.1% Tween 20-PBS was seeded into each well for blocking at 30° C. for 1 hour or longer. "GST-p53 C ter" and streptoavidin were dissolved in PBS to 20 μg/ml each. A sensitized plate was prepared in the same manner as in the case of the peptide substrate.

(3) Measurement Procedure

Liquid Phase Analysis System (Refer to FIG. 1)

The synthesized peptide substrates and a recombinant acetyltransferase were reacted in the liquid phase, and the enzyme activity was measured by the ELISA system using a microtiter plate. The peptide substrate (1.0 μg/ml) and the recombinant acetyltransferase (0 to 10 μg/ml) were added to the acetylation buffer (50 mM Tris-HCl, pH 8.0, 10% glycerol, 1 mM DTT, 1 mM PMSF, 10 mM sodium butyrate, 200 nM acetyl CoA), mixed, and reacted at 30° C. for 1 hour. One reaction was executed using a microtiter plate (acetyltransferase reaction) in 50 μl. After the reaction, each sample was transferred to a streptoavidin sensitized plate using a multichannel pipette (hereafter, a multichannel pipette was used for addition at each step), and incubated at 30° C. for 30 min to let the peptide substrate bind to the streptoavidin sensitized plate through biotin introduced at the amino ends. After incubation, each well was washed enough with the washing buffer (0.1% Tween 20, PBS) four times or more. Each anti-acetylated peptide specific antibody corresponding to each substrate was diluted with the antibody dilution buffer to 0.5 μg/ml, and 100 μl thereof was added to each washed well, and left at 30° C. for 1 hour (the first reaction). After the first reaction, each well was washed with the washing buffer in the same manner and 100 μl of goat anti-rabbit Ig (H+L) horse radish peroxidase label (MBL) diluted 3000 folds with the antibody dilution buffer was added thereto and further left at 30° C. for 1 hour (the second reaction). Each well was washed with the washing buffer, and 100 μl of horse radish peroxidase substrate solution was added to each well and incubated at 30° C. for 30 min for the coloring reaction. 100 μl of 1.5 N phosphate solution were added to terminate the coloring reaction, and absorbance at 450 nm was measured using a microtiter plate reader.

Figure 2:
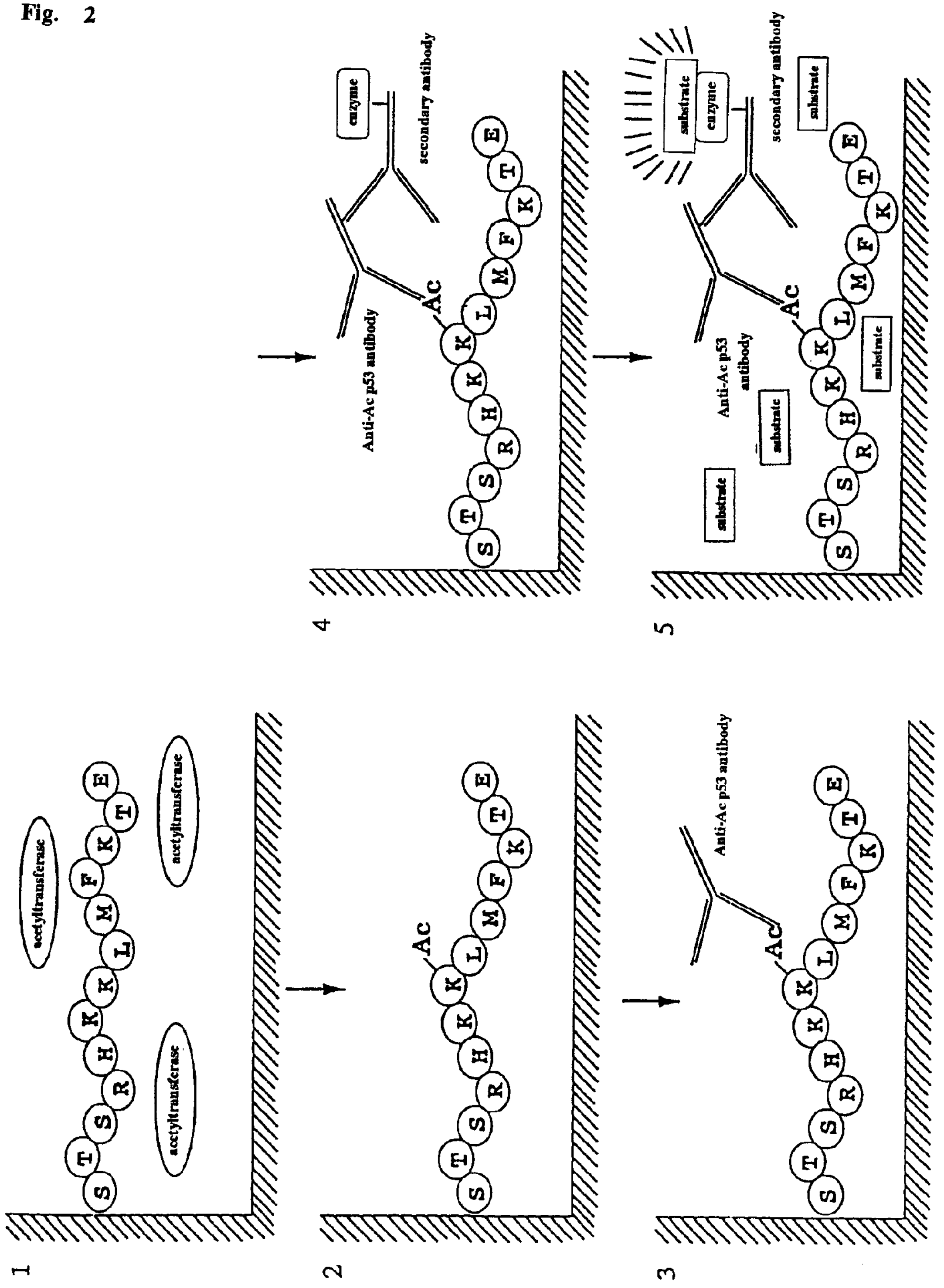
FIG. 2 shows the procedure (one example) of the solid phase analysis system for acetyltransferase activity using an anti-acetylated peptide antibody.

Solid Phase Analysis System (Refer to FIG. 2)

The acetyltransferase reaction was conducted in the well on which the peptide substrate and the recombinant GST-p53 P53 Cter were immobilized, and ELISA was performed on the same plate (basically after the first reaction, the procedure was same as in the liquid analysis system). To the acetylation buffer, each recombinant acetyltransferase was added to 0 to 10 μg/ml, and 50 μl each was added to the peptide substrate and the "GST-p53 Cter sensitized plate (the acetyltransferase reaction). After the reaction at 30° C. for 1 hour, each well was washed enough with the washing buffer four times or more. The anti-acetylated peptide specific antibody corresponding to each peptide substrate was diluted with the antibody dilution buffer to 0.5 μg/ml and 100 μl thereof was added to each washed well and left at 30° C. for 1 hour (the first reaction). After the first reaction, each well was washed with the washing buffer in the same manner and 100 μl of goat anti-rabbit Ig (H+L) horse radish peroxidase label (MBL) diluted 2000 folds with the antibody dilution buffer was added and further left at 30° C. for 1 hour (the second reaction). Each well was washed with the washing buffer, and 100 μl of horse radish peroxidase substrate solution was added to each well and incubated at 30° C. for 30 min for the coloring reaction. 100 μl of 1.5 N phosphate solution were added to terminate coloring reaction, and absorbance at 450 nm was measured using a microtiter plate reader.

(4) Result of measurement

Figure 9:
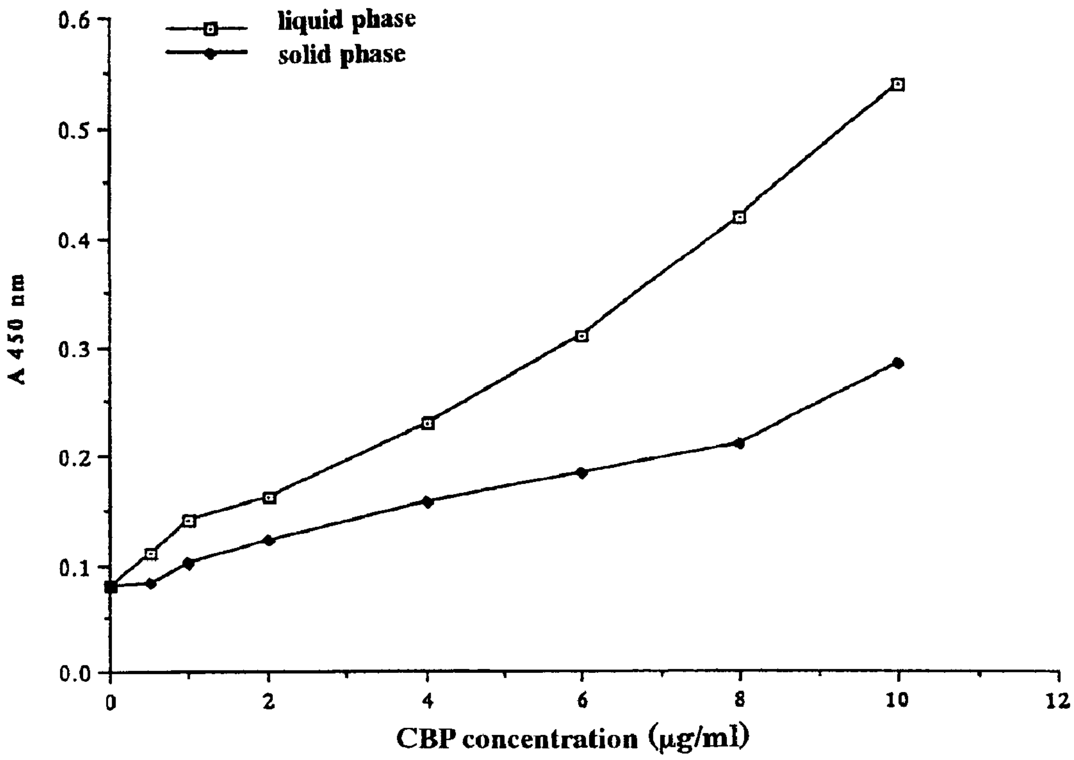
FIG. 9 shows the acetyltransferase activity against sub p53-1 of CBP.
Figure 10:
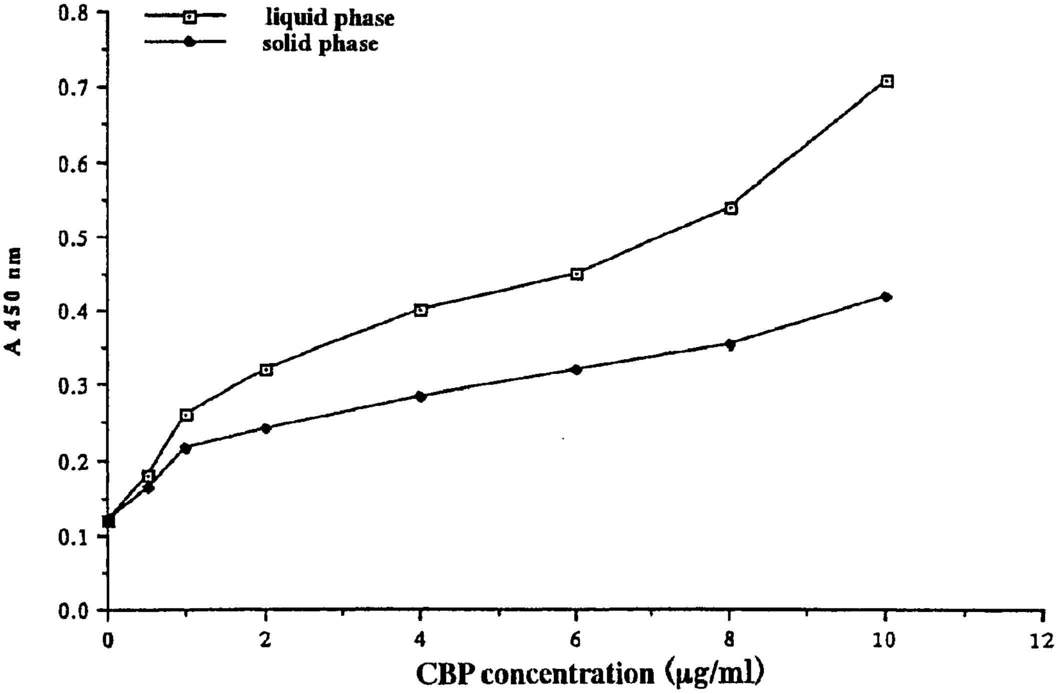
FIG. 10 shows the acetyltransferase activity against sub p53-2 of CBP.

FIGS. 9 and 10 show the results of measuring the acetyltransferase activity in the recombinant CBP using this ELISA method. The recombinant CBP purified from *E. coli* was added at a concentration of 0 to 10 μg/ml. "sub p53-1" and "sub p53-2" peptides (liquid phase), or peptide-sensitized plates of these (solid phase) were used. As a result, in liquid and solid phases, the acetyltransferase activities to "subp53-1" and "sub p53-2" peptides depending on the concentration of CBP were detected.

EXAMPLE 4

System for measuring the deacetylase activity

1. Construction of the ELISA system for measuring the deacetylase activity (most part of the basic manipulations were same as in the ELISA system for measuring the acetyltransferase activity)

(1) Preparation of a Peptide Substrate

Two peptide substrates "Sub Ac p53-1" (SEQ ID NO: 17/Bio-STSRHKK(Ac)LMFKTE and "Sub Ac p53-2" (SEQ ID NO: 18/Bio-SHLKSKK (Ac) GQSTSR) in which an acetyl group was introduced into the ϵ amino group on the 373rd and 382nd lysine residues of human p53, were prepared by a peptide synthesizer. An amino acid in a peptide is shown by the one-letter code and "Bio" at the amino ends means biotin. K(Ac) indicates an acetylated lysine residue. Ninety percent or higher purity of the synthesized peptides was confirmed by HPLC. "Sub Ac p53-1" and "Sub Ac p53-2" were composed of amino acid residues 376 to 388 and 367 to 379, of human p53, respectively.

(2) Preparation of a Peptide Substrate Sensitized Plate

Two peptides substrate were dissolved in PBS to 10 μg/ml. 50 μl of each peptide solution were added to each well on a microtiter plate for ELISA, and sensitized at 4° C. overnight. After sensitization, the peptide solution was removed and 200 μl of 1% BSA-0.1% Tween 20-PBS were added to each well, and blocking was effected at 30° C. for 1 hour or longer.

(3) Measurement Procedure

Figure 3:
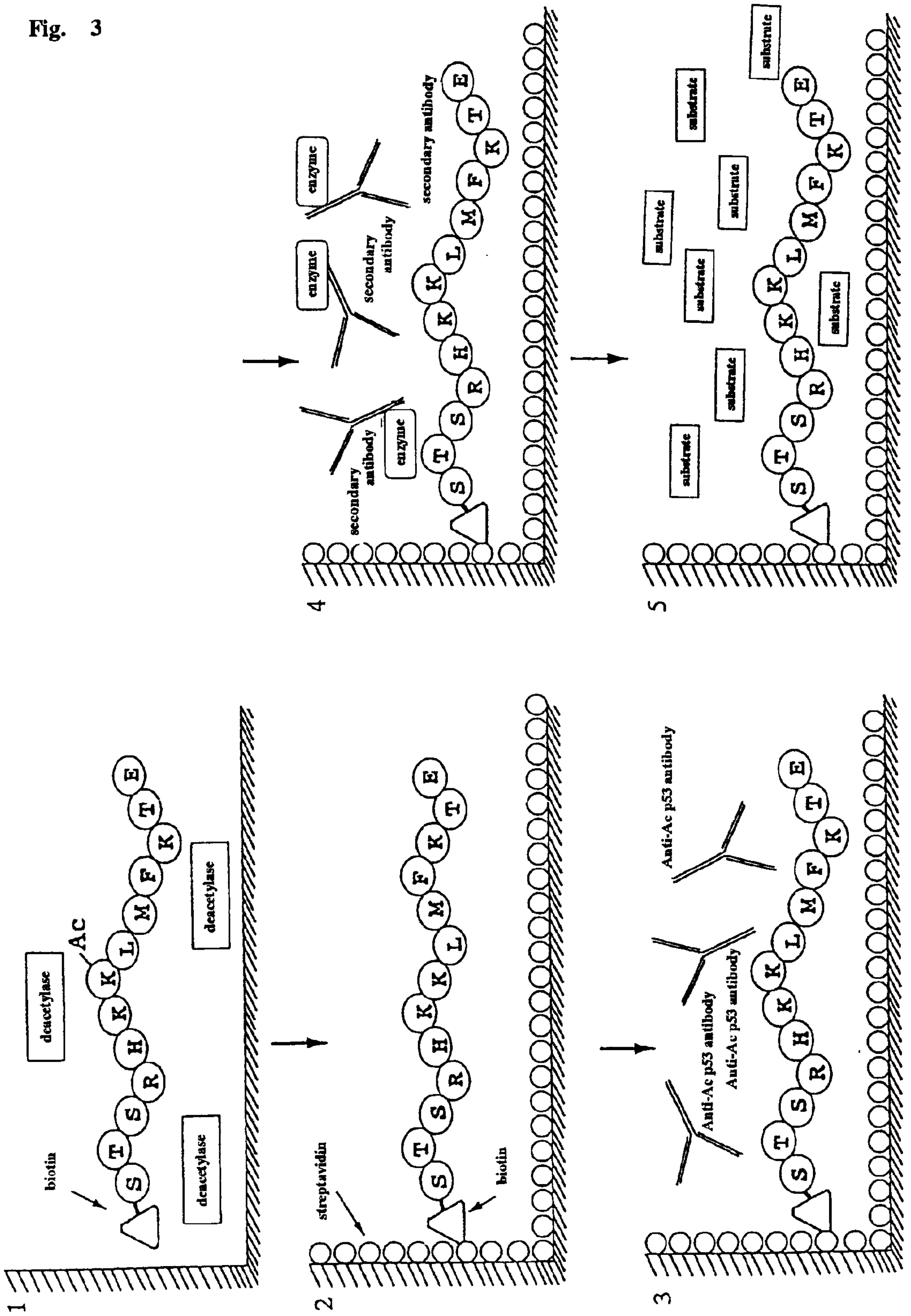
FIG. 3 shows the procedure (one example) of the liquid phase analysis system for deacetylase activity using an anti-acetylated peptide antibody.

Liquid Phase Analysis System (Refer to FIG. 3)

The synthesized peptide substrates and the recombinant deacetylase were reacted in the liquid phase, and the enzyme activity was measured by ELISA system using a microtiter plate. The peptide substrate (1.0 μg/ml) and the recombinant deacetylase (0 to 10 μg/ml) were added to the acetylation buffer (10 mM Tris-HCl pH 8.0, 10 mM EDTA, 150 mM NaCl), mixed, and reacted at 30° C. for 1 hour. One reaction was conducted using a microtiter plate (the deacetylase reaction) in 50 μl. After the reaction, each sample was transferred to a streptavidin sensitized plate with a multi-channel pipette (hereafter, a multichannel pipette was used for addition at each step), and incubated at 30° C. for 30 min to let the peptide substrate bind to the streptoavidin sensitized plate through biotin introduced at the amino ends. After incubation, each well was washed enough with the washing buffer (0.1% Tween 20, PBS) four times or more. The anti-acetylated peptide specific antibody corresponding to each peptide substrate was diluted with the antibody dilution buffer to 0.5 μg/ml and 100 μl thereof was added to each washed well, and left at 30° C. for 1 hour (the first reaction). After the first reaction, each well was washed with the washing buffer in the same manner and 100 μl of goat anti-rabbit Ig (H+L) horse radish peroxidase label (MBL) diluted 2000 folds with the antibody dilution buffer was added thereto and further left at 30° C. for 1 hour (the second reaction). The plate was washed with the washing buffer, and 100 μl of horse radish peroxidase substrate solution was added to each well and incubated at 30° C. for 30 min for the coloring reaction. 100 μl of 1.5 N phosphate solution were added thereto to terminate the coloring reaction, and absorbance at 450 nm was measured using a microtiter plate reader.

Figure 4:
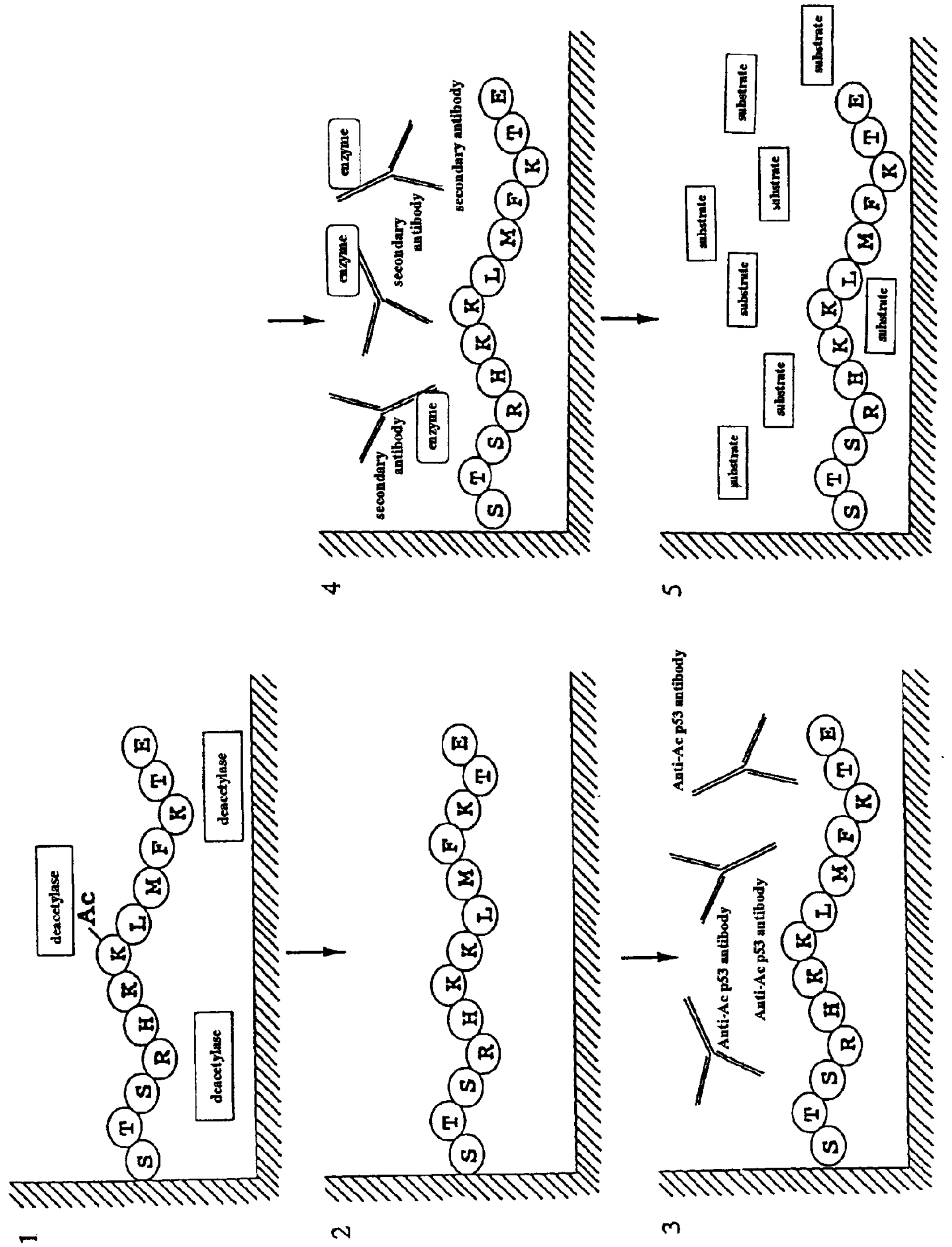
FIG. 4 shows the procedure (one example) of the solid phase analysis system for deacetylase activity using an anti-acetylated peptide antibody.

Solid Phase Analysis System (Refer to FIG. 4)

The deacetylase reaction was conducted in the well on which the peptide substrate was immobilized, and ELISA was subsequently performed in the same plate (basically after the first reaction, the procedure was same as in the liquid phase analysis system). The respective recombinant deacetylase (0 to 10 μg/ml) was added to the deacetylation buffer, and 50 μl each thereof was added to the peptide substrate sensitized plate (the deacetylase reaction). After the reaction at 30° C. for 1 hour, each well was washed enough with the washing buffer four times or more. The anti-acetylated peptide specific antibody corresponding to each peptide substrate was diluted with the antibody dilution buffer to 0.5 μg/ml, and 100 μl thereof was added to each washed well, and left at 30° C. for 1 hour (the first reaction). After the first reaction, each well was washed with the washing buffer and 100 μl of goat anti-rabbit Ig (H+L) horse radish peroxidase label (MBL) diluted 2000 folds with the antibody dilution buffer was added thereto and further left at 30° C. for 1 hour (the second reaction). The well was washed with the washing buffer, and 100 μl of horse radish peroxidase substrate buffer was added to each well and incubated at 30° C. for 30 min for the coloring reaction. 100 l of 1.5 N phosphate solution was added thereto to terminate the coloring reaction, and absorbance at 450 nm was measured using a microtiter plate reader.

(4) Results of measurement

Figure 11:
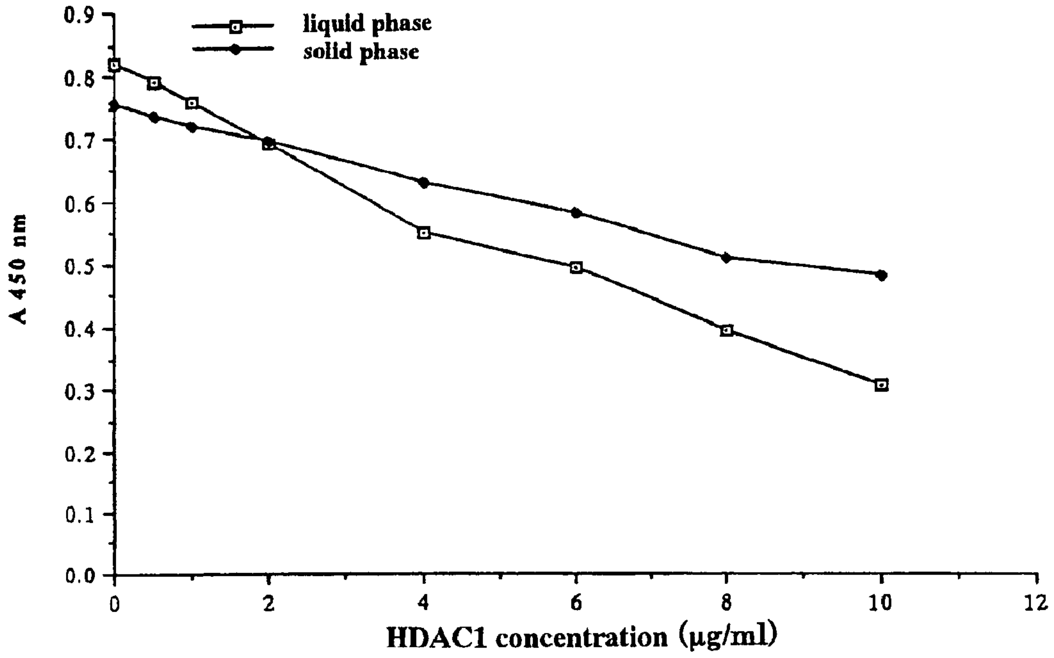
FIG. 11 shows the deacetylase activity against sub Ac p53-1 of HDAC1.
Figure 12:
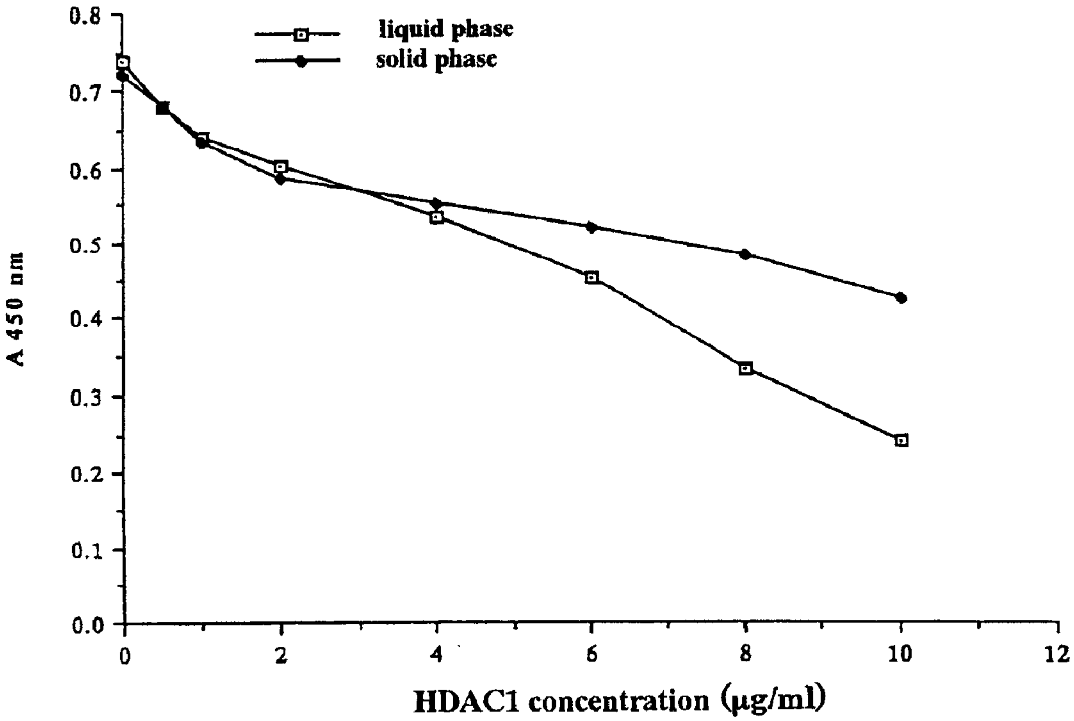
FIG. 12 shows the deacetylase activity against sub Ac p53-2 of HDAC1.

FIGS. 11 and 12 show the results of measuring the deacetylase activity in the recombinant HADC1 using this ELISA method. The recombinant HDAC1 purified from *E. coli* was added at a concentration of 0 to 10 μg/ml. "sub p53-1" and "sub p53-2" peptides (liquid phase), or peptide-sensitized plates of these (solid phase) were used. As a result, in liquid and solid phases, the deacetylase activities in "sub p53-1" and "sub p53-2" peptides depending on the concentration of HDAC1 were detected.

EXAMPLE 5

Detection of a Change in Acetylation in Histone in Cells Treated with Inhibitors for Histone Deacetylase 1. Preparation of an Antibody Against an Acetylated Lysine Residue As an immunogen, the synthetic peptide AcHistone-H4 (90% or higher purity; (SEQ ID NO: 19/SGRGK(Ac)GGK(Ac)GLGK(Ac)GGAK(Ac)RHRKC) ) including the acetylation site of histone H4 covalently bound to a carrier protein keyhole limpet hemocyanin (KLH) was used. The non-acetylated synthetic peptide, NonAcHistone-H4 (SEQ ID NO: 20/SGRGKGGKGLGKGGAKRHRKC) was prepared to use for absorbing an acetylation specific antibody.

2. Cell culture on a 96-Well Plate

Hela cells were spread onto a 96-well plate for cell culture by adjusting 2500 cells per well (culture medium was DMEM, 200 μl thereof was used per well), and cultured at 37° C. overnight in a 5% $CO_2$ incubator to tightly attach the cells onto the plate.

3. Treatment with known Inhibitors for Histone Deacetylase

Butyric acid and trichostatin A, known as inhibitors for histone deacetylase, were serially added to the medium to a final concentration of 0 to 10 mM, and of 0 to 2 μM, respectively and treated at 37° C. for 8 hours in a 5% $CO_2$ incubator.

4. Immobilization of cells on a plate

The medium was aspirated from each well without touching the cells, and each well was washed with 200 μl of PBS three times. After washing, 200 μl of 100% methanol cooled at −20° C. in advance was added to each well, left at room temperature for 5 min to fix the cells. Ethanol was completely aspirated and dried.

5. Detection of an acetylated peptide antibody

The anti-acetylated lysine residue antibody was diluted to 0.5 μg/ml with the antibody dilution buffer and 100 μl thereof was added to each washed well, and left at 30° C. for 1 hour (the first reaction). After the first reaction, each well was washed with the washing buffer in the same manner, and 100 μl of goat anti-rabbit Ig (H+L) horse radish peroxidase label (MBL) diluted 2000 folds with the antibody dilution buffer was added to each well, and left at 30° C. for 1 hour (the second reaction). Each well was washed with washing buffer, and 100 μl of horse radish peroxidase substrate solution was added to each well and incubated at 30° C. for 30 min for the coloring reaction. 100 μl of the 1.5 N phosphate solution was added thereto to terminate the coloring reaction. Absorbance at 450 nm was measured using a microtiter plate reader.

Figure 13:
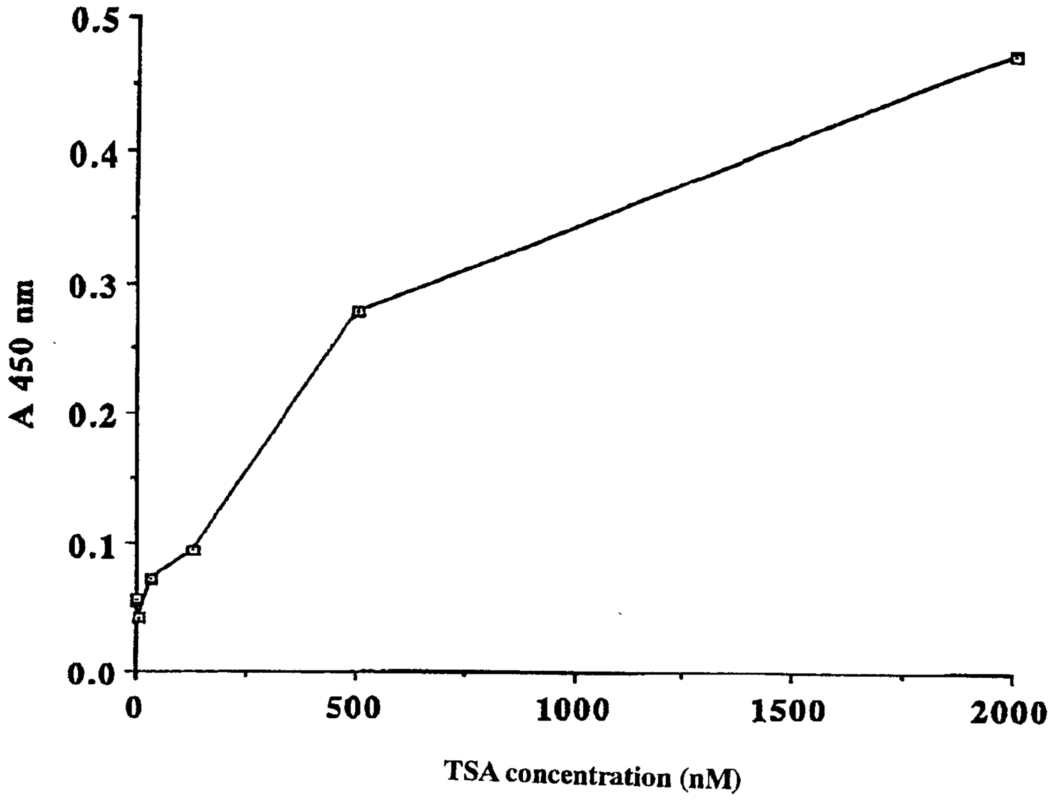
FIG. 13 shows the change in acetylation of histone in cells treated with various concentrations of the histone deacetylase inhibitor (trichostatin A/TSA) detected using an anti-acetylated lysine antibody.
Figure 14:
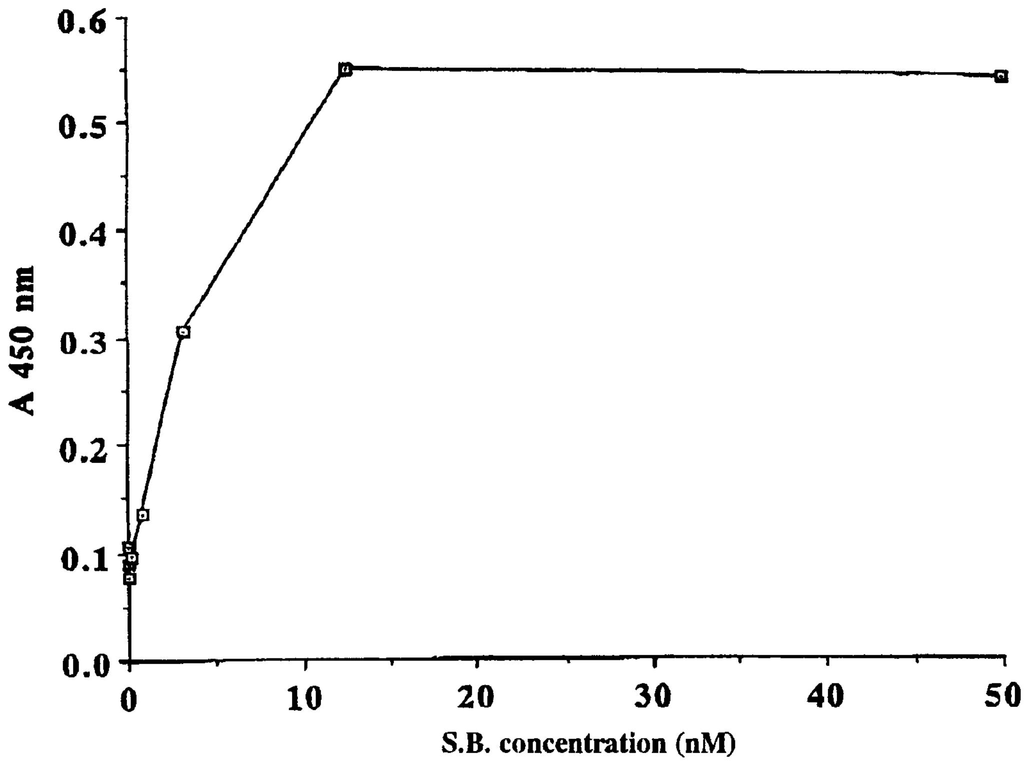
FIG. 14 shows the change in acetylation of histone in cells treated with various concentrations of the histone deacetylase inhibitor (butyric acid/S. B.), detected using an anti-acetylated lysine antibody.

As a result, an increase of absorbance was observed depending on the concentration of the deacetylase inhibitors (FIGS. 13 and 14, and Tables 1 and 2). In this measurement, a stronger inhibition of deacetylation of histone in cells accompanies a larger degree of acetylation of histone, and absorbance was increased depending on the increase in the concentration of antigen (an acetylated histone). Therefore, an inhibition of the deacetylase activity correlates to an increase of absorbance.

TABLE 1

| TSA concentration (nM) | Absorbance at 450 nm |
|---|---|
| 0 | 0.056 |
| 0.5 | 0.056 |
| 1.95 | 0.056 |
| 7.8 | 0.041 |
| 31.3 | 0.071 |
| 125 | 0.095 |
| 500 | 0.278 |
| 2000 | 0.476 |

TABLE 2

| S. B. concentration (mM) | Absorbance at 450 nm |
|---|---|
| 0 | 0.106 |
| 0.012 | 0.091 |
| 0.049 | 0.077 |
| 0.195 | 0.097 |
| 0.78 | 0.136 |
| 3.13 | 0.306 |
| 12.5 | 0.551 |
| 50 | 0.545 |

These examples indicated that changes in deacetylase or acetyltransferase activities can be detected by immobilizing the cultured cells treated with various reagents on a 96-well plate, and directly measuring the change in acetylation in proteins capable of being acetylated, such as histone, in these immobilized cells, by using an anti-acetylated peptide antibody. Therefore, by using this acetylation-deacetylation detection system, inhibitors of deacetylase and enhancers of expression and activation of acetyltransferase can be screened.

EXAMPLE 6

Detection of a Change in Activity of the Promotor Introduced into the Cultured Cells by the Treatment with Inhibitors for Deacetylase 1. Construction of a Plasmid Vector A plasmid vector (pcDNA3-GFP), in which GFP gene was introduced into a multicloning site immediately downstream of CMV promoter in pcDNA3 expression vector for mammalian cells in the forward direction was prepared by the standard method using *E. coli.*

2. Introduction of the Plasmid Vector into Cells and Screening of Plasmid-Harboring Cells pcDNA3-GFP was introduced into CHO cells by the lipofection method, and cultured for 24 hours at 37° C. in a 5% $CO_2$ incubator (4 ml of DMEM was used as a culture medium per 6 cm-plate). Neomycin, an antibiotic, the resistance gene of which is carried on pcDNA3 plasmid, was added to the medium, and cultured for 2 weeks to select cells harboring pcDNA3-GFP. During this screening, the medium was replaced with a new one containing neomycin every four days.

3. Screening of the Plasmid-Harboring Cells in which the Promoter Activity is Inhibited The clones of the screened cells were transferred to separate plates and cultured. These cells were observed with a fluorescence microscope. Several clones in which emission of the product of the GFP gene ligated downstream of CMV promoter was weak or was hardly detected were selected.

4. Culturing Cells on a 96-Well Plate

These cells were spread onto a 96-well plate for cell culture, adjusted to about 2500 cells per well (200 $\mu$l of DMEM was used as the culture medium per well), and cultured overnight (about 10 to 20 hours) at 37° C. in a 5% $CO_2$ incubator to tightly attach the cells onto the plate.

5. Treatment with known Inhibitors for Histone Deacetylase

Butyric acid and trichostatin A, known as inhibitors for histone deacetylase, were serially added to the medium, to a final concentration from 0 to 10 mM and 0 to 2 $\mu$M, respectively, and incubated for 8 hours at 37° C. in a 5% $CO_2$ incubator.

6. Measurement with a Fluorescent Multiplate Reader

The amount of GFP proteins expressing in cells in each well of the treated 96-well plate was measured with a fluorescent multiplate reader as change of fluorescence intensity.

Figure 15:
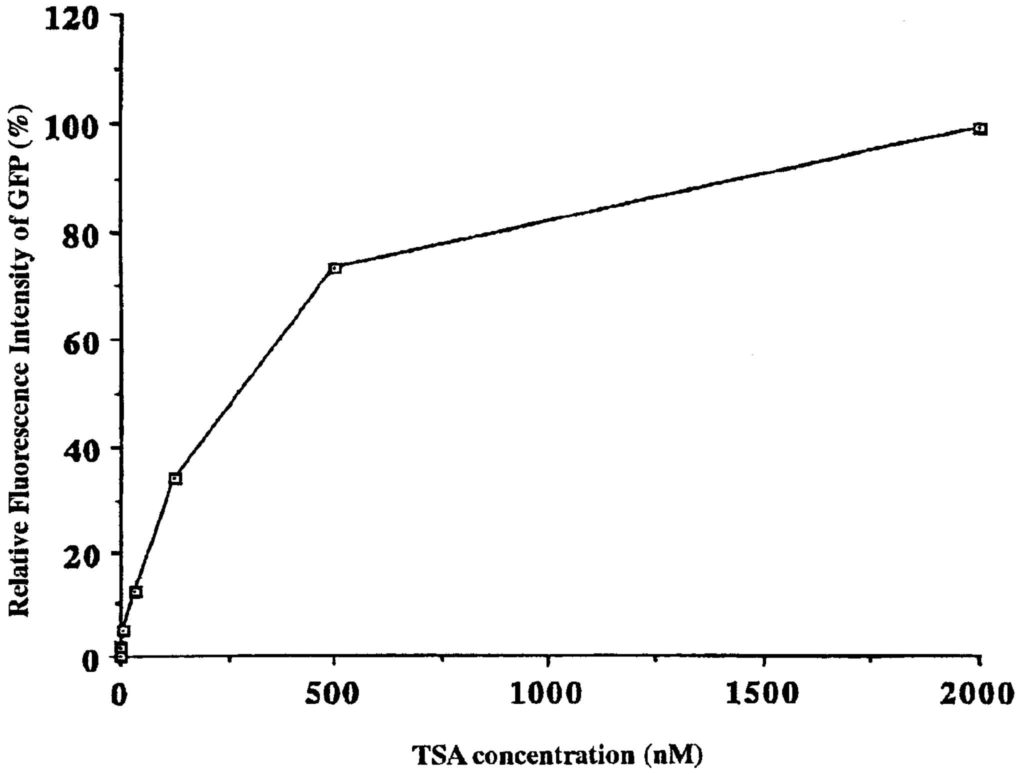
FIG. 15 shows the CMV promoter activity in cells treated with various concentrations of the histone deacetylase inhibitor (trichostatin A/TSA) detected using the reporter gene.
Figure 16:
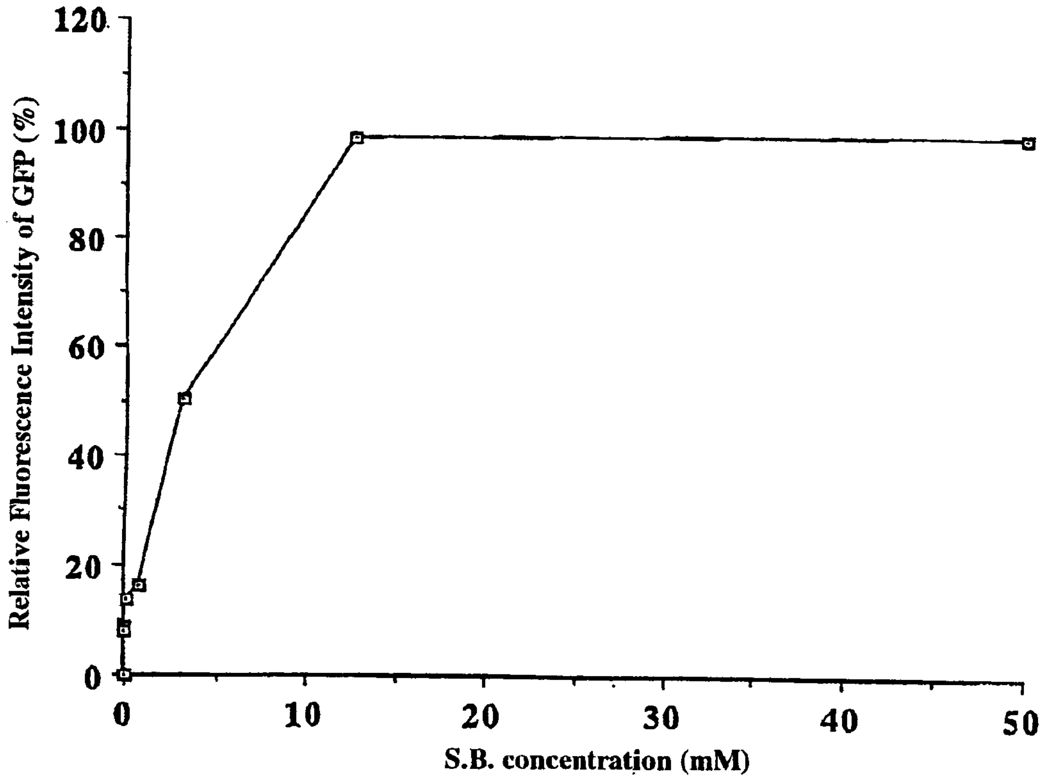
FIG. 16 shows the CMV promoter activity in cells treated with various concentrations of the histone deacetylase inhibitor (butyric acid/S. B.), detected using the reporter gene.

As a result, an increase of florescence intensity was observed depending on the concentration of the deacetylase inhibitors (FIGS. 15, 16 and Tables 3 and 4). As inhibition of the promoter activity is proposed to be managed by the deacetylation of histone, this result indicates that inhibition of the promoter is cancelled by the treatment with the deacetylase inhibitors, and expression of GFP protein was induced by the transcription of the gene downstream.

TABLE 3

| TSA concentration (nM) | Relative fluorescence intensity (%) |
|---|---|
| 0 | 0 |
| 0.5 | 2.2 |
| 1.95 | 1.8 |
| 7.8 | 5.1 |
| 31.3 | 12.3 |
| 125 | 34.2 |
| 500 | 73.1 |
| 2000 | 100 |

TABLE 4

| S. B. concentration (mM) | Relative fluorescence intensity (%) |
|---|---|
| 0 | 0 |
| 0.012 | 8.5 |
| 0.049 | 7.8 |
| 0.195 | 13.3 |
| 0.78 | 15.7 |
| 3.13 | 50.3 |
| 12.5 | 98.5 |
| 50 | 100 |

INDUSTRIAL APPLICABILITY

The present invention provides a method for detecting acetyltransferase and deacetylase activities by using an anti-acetylated peptide antibody. The conventional methods for detecting the acetyltransferase activity requires loading each sample on a filter and washing them for measurement of the activity after the enzyme reaction. The conventional methods for detecting deacetylase activity require separation and extraction of an acetyl group released in a reaction solution. In contrast, the method of detecting the acetyltransferase and deacetylase activities of the present invention is much more simple and convenient than the conventional methods as the enzyme reaction and the activity measurement can be successively conducted on the same well. Moreover, the method of the invention is outstanding in the points that a 96-well plate and instruments on the market can be used, thus, addition, washing and measurement of samples and antibodies can be automated.

The present invention also provides a method for screening inhibitors or enhancers of the acetyltransferase and deacetylase using the detection system utilizing the above anti-acetylated peptide antibody, and a method for screening inhibitors of deacetylase and enhancers of acetyltransferase using cultured cells. The above inhibitors or enhancers can be conveniently and efficiently screened by using these screening methods.

What is claimed is:

1. A method for screening a compound that inhibits or enhances activity of an acetyltransferase to catalyze a reaction that transfers an acetyl group from one substrate to another, the method comprising:

(a) contacting the acetyltransferase with a peptide substrate in a presence of a test compound, (b) detecting an amount of an acetylated peptide substrate using an anti-acetylated peptide antibody, wherein an effective amount of the anti-acetylated peptide antibody recognizes with specificity only an acetylated form of the peptide substrate and does not recognize the peptide substrate in its unacetylated form, (c) comparing the amount of the acetylated peptide substrate detected in step (b) with a control amount defined as an amount of an acetylated peptide substrate detected in an absence of the test compound, and (d) selecting the compound associated with an increase or decrease in the amount of the acetylated peptide substrate as compared to the control amount.

2. The method of claim 1 wherein the peptide substrate is p53.

3. The method of claim 1 wherein the peptide substrate is labeled.

4. The method of claim 3 wherein the label is biotin.

5. The method of claim 1 wherein the peptide substrate is immobilized on a solid phase.

6. The method of claim 1 wherein the anti-acetylated peptide antibody is labeled.

7. The method of claim 1 wherein the amount of the acetylated peptide substrate is detected by ELISA.

* * * * *

UNITED STATES PATENT AND TRADEMARK OFFICE

CERTIFICATE OF CORRECTION

PATENT NO. : 6,884,597 B1
DATED : April 26, 2005
INVENTOR(S) : Y. Taya et al.

It is certified that error appears in the above-identified patent and that said Letters Patent is hereby corrected as shown below:

Title page,
Item [75], Inventors, please correct "Katsuyuki Tamai, Ina (JP)" to -- Katsuyuki Tamai, Nagano (JP) -- and please correct "Toshiaki Miyazaki, Ina (JP)" to -- Toshiaki Miyazaki, Nagano (JP) --
Item [56], References Cited, OTHER PUBLICATIONS, please correct "Muller et al., Molec. Immun., 24:779-789 (1993)" to -- Muller et al., Molec. Immun., 24:779-789 (1987) -- and please correct "Schekman et al., Cell, 87:595-595 (1996)" to -- Schekman et al., Cell, 87:593-595 (1996) --

Signed and Sealed this

Ninth Day of August, 2005

JON W. DUDAS
*Director of the United States Patent and Trademark Office*